(12) United States Patent
Raynel et al.

(10) Patent No.: US 11,845,902 B2
(45) Date of Patent: Dec. 19, 2023

(54) ONLINE ANALYSIS IN A GAS OIL SEPARATION PLANT (GOSP)

(71) Applicant: Saudi Arabian Oil Company, Dhahran (SA)

(72) Inventors: Guillaume Robert Jean-Francois Raynel, Dhahran (SA); Debora Salomon Marques, Dhahran (SA); Qasim Saleem, Al Khobar (SA); Tim Benson, Abingdon (GB)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/909,430

(22) Filed: Jun. 23, 2020

(65) Prior Publication Data
US 2021/0395619 A1 Dec. 23, 2021

(51) Int. Cl.
| | |
|---|---|
| *C10G 33/08* | (2006.01) |
| *C10G 7/02* | (2006.01) |
| *C10G 7/06* | (2006.01) |
| *C10G 53/02* | (2006.01) |
| *G01N 24/08* | (2006.01) |
| *G01N 33/18* | (2006.01) |

(52) U.S. Cl.
CPC .............. *C10G 33/08* (2013.01); *C10G 7/02* (2013.01); *C10G 7/06* (2013.01); *C10G 53/02* (2013.01); *G01N 24/082* (2013.01); *G01N 24/085* (2013.01); *G01N 33/18* (2013.01); *C10G 2300/201* (2013.01)

(58) Field of Classification Search
CPC . C10G 33/08; C10G 7/02; C10G 7/06; C10G 53/02; C10G 2300/201; G01N 24/082; G01N 24/085; G01N 33/18
See application file for complete search history.

(56) References Cited

U.S. PATENT DOCUMENTS

| | | | | |
|---|---|---|---|---|
| 2,221,518 | A * | 11/1940 | Jennings | ................ C10G 33/06 516/196 |
| 2,273,915 | A * | 2/1942 | Wellman | ................ C10G 33/06 516/197 |
| 3,546,926 | A | 12/1970 | Dunavent, Jr. et al. | |
| 3,784,461 | A * | 1/1974 | Kusovsky | .............. C10G 33/08 204/672 |

(Continued)

FOREIGN PATENT DOCUMENTS

| | | |
|---|---|---|
| CN | 104520411 | 4/2015 |
| EP | 0230683 B1 | 8/1987 |

OTHER PUBLICATIONS

Foruny, Measuring Salinity in crude oils: Evaluation of methods and an improved performance, 2008, Fuel, 1241-1248 (Year: 2008).*

(Continued)

*Primary Examiner* — Michelle Stein
(74) *Attorney, Agent, or Firm* — Fish & Richardson P.C.

(57) ABSTRACT

A gas oil separation plant (GOSP) and method for receiving crude oil from a wellhead and removing gas, water, and salt from the crude oil, and discharging export crude oil. The GOSP includes online analyzer instruments for performing online analysis of salt concentration in multiple streams in the GOSP. Based in part on the online analysis, the salt content in the export crude oil may be determined and the flowrate for wash water supplied to the desalter vessel may be specified.

24 Claims, 12 Drawing Sheets

(56) References Cited

U.S. PATENT DOCUMENTS

| | | | |
|---|---|---|---|
| 4,543,191 A | 9/1985 | Stewart et al. | |
| 4,581,134 A * | 4/1986 | Richter, Jr. | B01D 17/0214 |
| | | | 210/96.1 |
| 4,742,304 A | 5/1988 | Schnall et al. | |
| 5,089,781 A | 2/1992 | Arichika et al. | |
| 6,364,940 B1 | 4/2002 | Prueter et al. | |
| 8,115,481 B2 | 2/2012 | Chen | |
| 8,197,673 B2 | 6/2012 | Khan | |
| 8,790,509 B2 | 7/2014 | Vu | |
| 8,805,587 B1 | 8/2014 | Elshafei et al. | |
| 9,092,124 B2 | 7/2015 | Amminudin et al. | |
| 9,295,957 B2 | 5/2016 | Choi et al. | |
| 9,493,712 B2 | 11/2016 | Barroeta et al. | |
| 9,555,345 B2 | 1/2017 | Al-Shafei et al. | |
| 9,861,910 B2 | 1/2018 | Hammad et al. | |
| 10,260,010 B2 | 4/2019 | Soliman | |
| 10,472,576 B2 | 11/2019 | Salu et al. | |
| 10,513,663 B2 | 12/2019 | Soliman et al. | |
| 11,148,962 B2 * | 10/2021 | Alghunaimi | B01D 71/02 |
| 2008/0149483 A1 * | 6/2008 | Robison | G01N 27/407 |
| | | | 264/275 |
| 2008/0221226 A1 * | 9/2008 | Coutinho | C10G 32/02 |
| | | | 516/194 |
| 2009/0179636 A1 * | 7/2009 | Chen | G01R 33/3808 |
| | | | 324/303 |
| 2013/0024026 A1 * | 1/2013 | Prasad | G01F 23/2962 |
| | | | 700/272 |
| 2013/0026082 A1 * | 1/2013 | Al-Shafei | C10G 33/02 |
| | | | 210/96.1 |
| 2014/0131254 A1 * | 5/2014 | Soliman | C10G 31/08 |
| | | | 208/187 |
| 2014/0198898 A1 * | 7/2014 | Beumer | G01N 33/2823 |
| | | | 378/47 |
| 2014/0262953 A1 * | 9/2014 | Ng | C08F 8/32 |
| | | | 208/188 |
| 2015/0106027 A1 | 4/2015 | Koseoglu et al. | |
| 2015/0361350 A1 * | 12/2015 | Prasad | G01F 23/2962 |
| | | | 700/285 |
| 2017/0254793 A1 * | 9/2017 | Al-Amri | G01N 33/2835 |
| 2017/0369791 A1 * | 12/2017 | Khan | C10G 31/06 |
| 2018/0187095 A1 * | 7/2018 | Soliman | B03C 11/00 |
| 2018/0195010 A1 * | 7/2018 | Salu | C10G 31/08 |
| 2018/0291282 A1 * | 10/2018 | Soliman | C10G 31/08 |
| 2018/0371876 A1 * | 12/2018 | Lopez | B01D 17/047 |
| 2019/0062645 A1 * | 2/2019 | Al Seraihi | B01D 17/047 |

OTHER PUBLICATIONS

Neisi, Effect of Mixing Efficiency in Dilution Water Consumption in a Crude Oil Desalting Plant, 2011, 3rd International Conference on Chemical, Biological and Environmental Engineering, vol. 20, 109-113. (Year: 2011).*

PCT International Search Report and Written Opinion in International Appln. No. PCT/US2021/038708, dated Oct. 5, 2021, 12 pages.

* cited by examiner

ONLINE ANALYSIS IN A GAS OIL SEPARATION PLANT (GOSP)

TECHNICAL FIELD

This disclosure relates to crude oil monitoring and desalter wash-water control in a gas oil separation plant (GOSP).

BACKGROUND

A gas oil separation plant (GOSP) may be a system employed to process crude oil received from a wellhead. The crude oil received may be obtained via the wellhead from a hydrocarbon-bearing reservoir in a subterranean formation. The GOSP may have a train of vessels that operate at sequentially lower pressure to remove volatile gases, water, and salt from the crude oil. The GOSP may discharge the processed crude oil as export crude oil (product crude oil) for distribution including to storage and transportation for further processing, such as in a petroleum refinery. The GOSP may have a stabilizer distillation column integrated or as separate facility to remove gases to lower vapor pressure of the crude oil to stabilize the crude oil. The stabilizer distillation column may remove hydrogen sulfide from the crude oil to sweeten the crude oil.

The crude oil received at the GOSP from the wellhead typically includes produced water. Therefore, the crude oil may be a tight emulsion of oil and water. The emulsion may include water droplets dispersed in a continuous phase of oil. Moreover, emulsifying agents utilized in the upstream production of the crude oil may be present in the crude oil received at the GOSP. The produced water in the crude oil (emulsion) may be salty water produced along with the crude oil. Thus, the crude oil received at the GOSP may be an oil-water emulsion and have salt in the water in the emulsion. The salt may be sodium chloride (NaCl) but also can include, for example, calcium chloride ($CaCl_2$)) and magnesium chloride ($MgCl_2$). The salt in crude oil streams may generally be salt in brine droplets in the crude oil stream.

Wash water (e.g., fresh water) may be employed in the GOSP desalting to facilitate the removal of salt to lower the salt content of the crude oil (e.g., export crude oil) to specification or below specification. The removal of salts from the crude oil may be promoted by washing the crude oil with the wash water to reduce (dilute) the concentration of dissolved salt in the water droplets in the crude oil and, hence, reduce salt content in the outgoing crude. In some instances, produced crude oil (export crude oil) from GOSPs should generally have a salt content of less than, for example, 10 pounds per thousand barrels (PTB) to be acceptable to certain international crude buyers.

SUMMARY

An aspect relates to a method of operating a gas oil separation plant (GOSP). The method includes receiving crude oil from a wellhead and removing gas, water, and salt from the crude oil via a GOSP train. The GOSP train includes a first production trap, a second production trap, a dehydrator vessel, and a desalter vessel. The method includes discharging export crude oil from the desalter vessel. The method includes performing online analysis of salt concentration in streams in the GOSP, and determining a salt mass balance of the GOSP based on the online analysis.

Another aspect relates to a method of operating a GOSP, including removing gas, water, and salt from crude oil via a GOSP train having a first production trap, a second production trap, a dehydrator vessel, and a desalter vessel. The method includes discharging export crude oil from the desalter vessel. The method includes determining salt concentration in water in streams in the GOSP based on online analysis of the salt concentration in the water in the streams. The method includes specifying a flowrate for wash water supplied to the desalter vessel correlative with a specified salt content for the export crude oil and correlative with the salt concentration in the water in the streams as determined.

Yet another aspect relates to a method of operating a GOSP, including removing gas, water, and salt from crude oil via a GOSP train having a first production trap, a second production trap, a dehydrator vessel, and a desalter vessel. The method includes performing online analysis of salt concentration on multiple streams in the GOSP. The method includes determining salt content in export crude oil discharged from the desalter vessel correlative with the salt concentration for the multiple streams as determined via the online analysis.

Yet another aspect relates to GOSP including a first production trap to receive crude oil from a wellhead and remove gas and water from the crude oil. The first production trap has an outlet to discharge a first water stream into a first conduit. The GOSP includes a first online analyzer instrument disposed along the first conduit to determine a first salt concentration in the first water stream. The GOSP includes a second production trap to receive the crude oil from the first production trap and remove gas from the crude oil. The GOSP includes a dehydrator vessel to receive the crude oil from the second production trap and remove water from the crude oil. The dehydrator vessel has an outlet to discharge a second water stream into a second conduit. The GOSP includes a second online analyzer instrument disposed along the second conduit to determine a second salt concentration in water in the second water stream. The GOSP includes a desalter vessel to receive the crude oil from the dehydrator vessel and remove water comprising salt from the crude oil and discharge export crude oil. The GOSP may include a third conduit to convey wash water to the desalter vessel, and a third online analyzer instrument disposed along the third conduit to determine a third salt concentration in the wash water.

The details of one or more implementations are set forth in the accompanying drawings and the description below. Other features and advantages will be apparent from the description and drawings, and from the claims.

DETAILED DESCRIPTION

Aspects of the present disclosure are directed to operation of a gas oil separation plant (GOSP). Some aspects are directed to online analytical equipment in the GOSP. The disclosure relates to the monitoring of quality of crude oil (e.g., export crude) discharged from the GOSP via calculation (e.g., in real-time) of the salt content in the discharged crude oil. The salt content in the export crude oil may be calculated as correlative with salt concentrations in water in GOSP streams measured via online analysis. Further, the disclosure relates to specifying (e.g., in real time) the flowrate of wash water entering a GOSP desalter vessel correlative with the salt concentrations in streams measured via the online analysis.

Embodiments of the present techniques may measure and quantify the amount of sodium in water in multiple streams in the GOSP via online analysis in real time to: (1) determine in real time the salt content in the export crude oil (and thus determine if the export crude oil is in specification with respect to salt content); and (2) automate specifying the flowrate of wash water to the desalter to maintain the export crude oil in specification with respect to salt content. The salt content of the export crude oil, as well as the flowrate of the wash water to specify, may be calculated by a control system based on a GOSP salt mass balance(s) determined by the control system in real time utilizing online data for streams in the GOSP.

Embodiments of the GOSP may include two-stage desalting involving the dehydrator and the desalter. The salt in crude oil streams may generally be salt in brine droplets in the crude oil streams.

Figure 1:
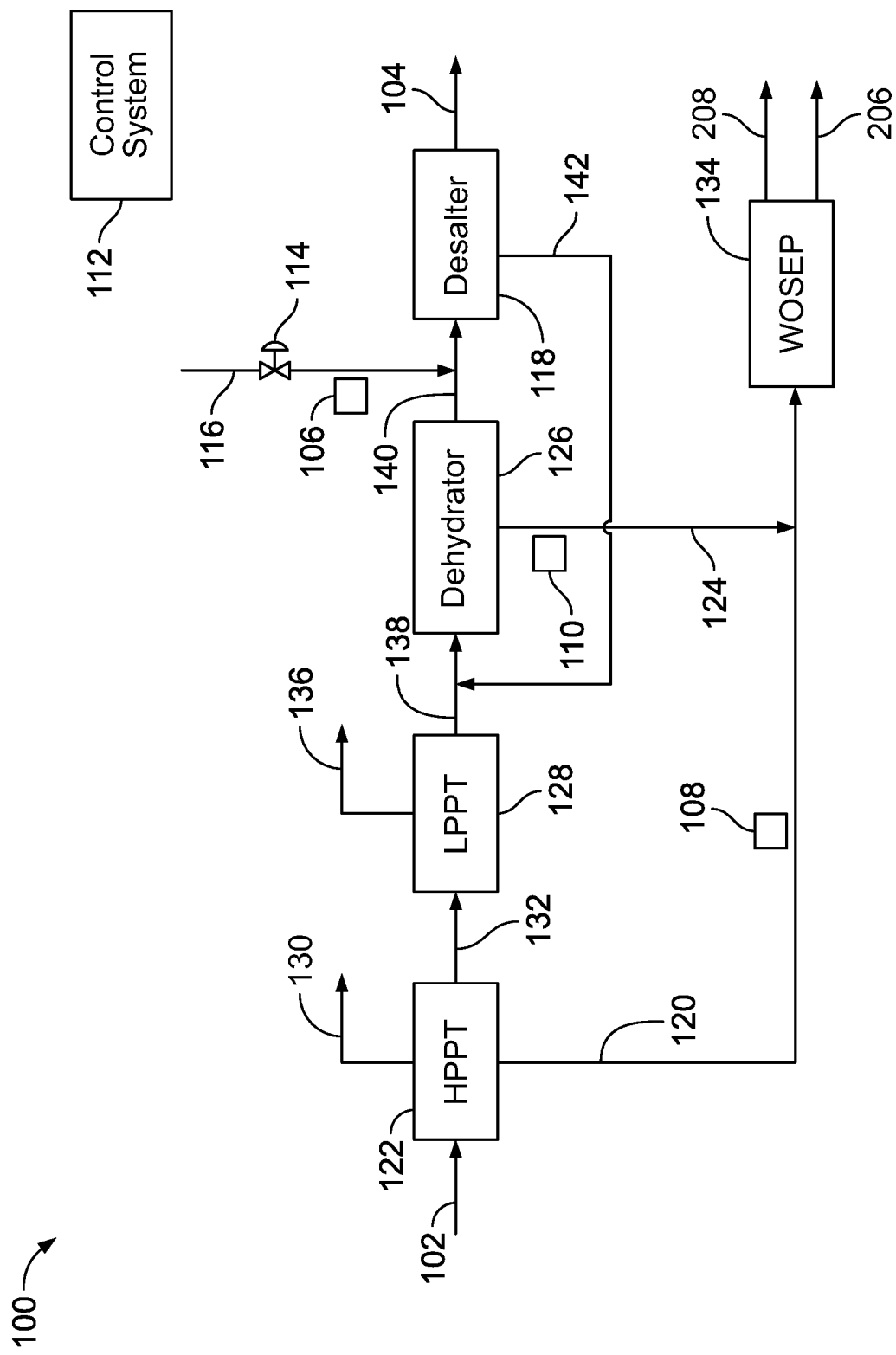
FIG. 1 is a block flow diagram of a gas oil separation plant (GOSP) that processes crude oil received from wellheads and discharges export crude oil as product.

FIG. 1 is a GOSP 100 that processes crude oil 102 received from a wellhead and discharges export crude oil 104 as product. As discussed below, the GOSP 100 removes salt from the crude oil 102. The salt is dissolved in the fine water droplets in the crude oil 102 and generally not in the crude oil 102 itself. The salt may typically be sodium chloride (NaCl) but can also include calcium chloride ($CaCl_2$)) and magnesium chloride ($MgCl_2$). The GOSP 100 includes multiple analyzer instruments (e.g., 106, 108, 110, etc.) to measure salt concentration of streams internal in the GOSP 100 such that the salt concentration in the export crude 104 can be calculated. The analyzer instruments may measure sodium to give the salt concentration as based on sodium chloride (NaCl). The control system 112 (or computer system) can perform a mass balance to determine (calculate) salt content in the export crude oil 104 based on the measurements by the analyzer instruments. In view of the measurements by the analyzer instruments, the control system 112 may direct the flowrate set point of the flow control valve 114 (or wash-water pump) that controls the flowrate of the wash water 116 supplied to the desalter 118 vessel.

The multiple analyzer instruments (e.g., 106, 108, 110, etc.) may each be an online analyzer instrument (analyzer tool) to measure concentration of salt (e.g., NaCl) in water in a stream. The online analyzer instrument may be disposed along a conduit conveying the stream. The illustrated embodiment includes at least three such online analyzer instruments that measure salt (NaCl) concentration: (1) online analyzer instrument 106 (e.g., analogous to 418 in FIG. 4) that measures salt concentration in the wash water 116; (2) online analyzer instrument 108 (e.g., analogous to 410 in FIG. 4) that measures salt concentration in the water 120 that discharges from the high-pressure production trap (HPPT) 122; and (3) online analyzer instrument 110 (e.g., analogous to 412 in FIG. 4) that measures salt concentration in the water of the oily water 124 that discharges from the dehydrator 126 vessel. The analytical techniques, mass balances, and control schemes are discussed below with respect to subsequent figures.

The feed crude oil 102 received at the GOSP 100 from a well may be as produced from a subterranean formation through a wellbore (and production manifold) to the GOSP 100. The feed crude oil 102 may flow through a production manifold associated with one or more wellheads to the GOSP 100. The feed crude oil 102 may be from a well pool. The feed crude oil 102 may include water and thus be labeled as wet crude oil. The feed crude oil 102 received at the GOSP 100 may be a tight emulsion of oil and water in some examples. A tight emulsion is generally an emulsion with small and closely distributed droplets.

The GOSP 100 removes gas, water, and salt from the crude oil 102. The GOSP 100 may remove hydrocarbons as gas from the crude oil via lowering pressure of the crude oil 102. The removed hydrocarbons may be light hydrocarbons (e.g., C1 to C4) and medium or heavier hydrocarbons (e.g., C5+).

In the illustrated implementation, the GOSP 100 includes the HPPT 122, a low-pressure production trap (LPPT) 128, the dehydrator 126, and the desalter 118. The HPPT 122, LPPT 128, dehydrator 126, and desalter 118 may be characterized as components of a GOSP 100 train. The HPPT 122, LPPT 128, dehydrator 126, and desalter 118 are each a separator vessel that may have a horizontal orientation or vertical orientation. In embodiments, the HPPT 122, LPPT 128, dehydrator 126, and desalter 118 are all horizontal vessels. In certain examples, the HPPT 122 vessel, LPPT 128 vessel, dehydrator 126 vessel, and desalter 118 vessel each have elliptical-type heads.

The HPPT 122 vessel, LPPT 128 vessel, dehydrator 126 vessel, and desalter 118 vessel generally include nozzles (e.g., flanged, screwed connections, etc.) on the vessel body or heads to couple to conduits for receiving and discharging streams. An inlet on the vessel may be a nozzle that couples to a feed or supply conduit to the vessel. An outlet on the vessel may be a nozzle that couples to a discharge conduit from the vessel. Nozzles on the vessels may also be employed for instrumentation (e.g., sensors, gauges, transmitters, etc.) and other uses.

In operation, the HPPT 122 may receive the feed crude oil 102 via a conduit. The HPPT 122 as a separation vessel may provide for a three-phase separation. In particular, the HPPT 122 separates gas 130 and water 120 from the feed crude oil 102 and discharges crude oil 132. This HPPT water 120 discharge stream is generally not oily due to the fact that there is typically a constant water level in the HPPT 122, which keeps the oil droplets at the interface, not in the bulk. The HPPT 122 vessel may include an inlet separation device to promote separation of the gas 130 and water 120 from the feed crude oil 120. The inlet separation device may promote an initial gross separation by changing the flow direction of the feed crude oil 102 entering the HPPT 122 vessel. The inlet separation device may be, for example, an inlet diverter. The inlet diverter can be a splash plate, inlet deflector, deflector baffle, or baffle plate(s). The inlet diverter as a baffle plate can be a spherical dish, flat plate, angle iron, or another type of structural steel. The inlet diverted can be a half sphere, cone, or centrifugal diverter, and so on.

The HPPT 122 as a three-phase separator vessel may utilize gravity or density difference to separate the water 120 from the crude oil 132. For instance, the HPPT 122 vessel may include a weir to facilitate the separation in which the oil (the lighter of the two liquids) overflows the weir. The water 120 may generally discharge from within the weir. The separated water 120 may be sent, for example, to a water/oil separator (WOSEP) 134 vessel. The WOSEP 134 may discharge a water stream 208 and a recovered oil stream 208. In implementations, the operating pressure in the HPPT 122 may be at least 150 pounds per square inch gauge (psig). The operating temperature in the HPPT 122 may be, for example, at least about 65° F., or in a range of 65° F. to 150° F.

The separated gas 130 that discharges from the HPPT 122 may generally be light hydrocarbons. The feed crude oil 102 is reduced in pressure in the HPPT 122 to separate the gas 130. In embodiments, the gas 130 may be light hydrocarbons (C1-C4) having a number of carbons in the range 1 to 4 and trace amount of C5+ hydrocarbons having five or more carbons. In examples, the gas 130 as a light (or lighter) hydrocarbon stream may generally be C1-C4 components (e.g., methane, ethane, propane, butane, isobutane) and trace amounts of C5+ compounds. The pressure of the gas 130 as discharged may range in pressure, for example, from 150 psig to 450 psig depending, for instance, on the supply pressure of the feed crude oil 102. The gas 130 can include lighter hydrocarbons, traces of C5+ hydrocarbons, hydrogen sulfide ($H_2S$), carbon dioxide ($CO_2$), nitrogen ($N_2$), and water vapor. The relative amounts and types of compounds in the gas 130 may typically depend on composition of the feed crude oil 102 and the flash pressure in the HPPT 122. The separated gas 130 may be sent to a mechanical compressor or to a gas plant for recovery.

The crude oil 132 is discharged from the HPPT 122 via a conduit to the LPPT 128. The motive force for flow of the crude oil 132 may be pressure differential. The LPPT 128 operates at a lower pressure than the HPPT 122. In implementations, the operating pressure in the LPPT 128 may be less than 50 psig. The operating temperature of the LPPT 128 may be, for example, at least about 65° F., or in a range of 65° F. to 150° F. The LPPT 128 vessel may include an inlet diverter to promote an initial gross separation of gas 136 from the crude oil 132 by changing the flow direction of the entering crude oil 132.

The LPPT 128 may be characterized as a two-phase separation vessel or three-phase separation vessel. The LPPT 128 separates gas 136 (e.g., certain remaining off-gases) from the crude oil 132 and discharges a crude oil 138 stream. The gas 136 may typically be heavier hydrocarbons. The medium or heavy hydrocarbon stream as the gas 136 may refer generally to C5+(five-carbon and greater) hydrocarbons (e.g., pentane, isopentane, hexane, and heptane) and trace amounts of lighter hydrocarbons and other light components. In certain examples, the gas 136 may discharge at a pressure of, at least 50 psig, or in a range of 40 psig to 60 psig. The gas 136 may be sent to a mechanical compressor or gas compression plant for recovery.

The crude oil 138 discharged from the LPPT 128 may be labeled as de-gassed and de-watered crude oil. The crude oil 138 may be sent to the dehydrator 126. In implementations, the crude oil may be pumped from the LPPT 128 to the dehydrator 126 via a pump (not shown). The pump may be, for example, a centrifugal pump or positive displacement pump. In certain implementations, the crude oil 138 may flow through a heat exchanger (not shown) to heat the crude oil 138. The heat exchanger may be, for example, a shell-and-tube heat exchanger, a plate-and-frame heat exchanger, etc. In operation, the pump head provides motive force for flow of the crude oil 138 through the heat exchanger to the dehydrator 126. The heat exchanger heats the crude oil 138 to advance downstream separation of water and salt from the crude oil. This increase in temperature of the crude oil 138 may promote coalescence and settling of water droplets from the crude oil in downstream processing. The heat transfer fluid for the heat exchanger may be, for example, steam or steam condensate, or a process stream (e.g., crude oil). The crude oil 138 may be heated in the heat exchanger via cross-exchange with other crude oil to recover heat from the other crude oil. In some embodiments, a low-pressure degassing tank (LPDT) (not shown) may be operationally disposed between the LPPT 128 and the dehydrator 126, such as between the heat exchanger (if employed) and the dehydrator 126. An LPDT may be employed, for example, in cases of the system 100 that will flash the crude oil in a stabilizing distillation column downstream of the desalter 118.

In the dehydrator 126 vessel, water 124 is separated from the crude oil 138. Salt may discharge in the water 124 and thus be removed from the crude oil 140. Electrostatic coalescence may be employed in the dehydrator 126. In implementations, an electrostatic field is generated between electrodes in the dehydrator 126 vessel. Electrostatic coalescence applies an electric current, causing water droplets in the crude oil (emulsion) to collide, coalesce into larger (heavier) drops, and settle out of the crude oil as separate liquid water. This process partially dries wet crude oil. In one example, operating conditions of a dehydrator 126 unit include temperature in a range of 70° F. to 160° F., and a pressure at about 25 psig above the crude oil 140 vapor pressure. In some examples, fresh or recycle wash water (e.g., relatively low in salt) and/or chemicals may be injected into the dehydrator 126 vessel to advance separation of the water 124 from the crude oil 138. The separated water 124 discharged from the dehydrator 126 may be oily water (e.g., having salt) and sent to the WOSEP 134 vessel. In examples, oily water may have less than 10 volume percent oil. The dehydrator 126 vessel may discharge crude oil 140 via a conduit to the desalter 118 vessel. The crude oil 140 may be labeled as dehydrated crude oil with some salt removed in implementations.

The salt removal in the GOSP 100 can be multi-stage. Both the desalter 118 and the dehydrator 126 may provide for salt removal. Thus, the embodiment of FIG. 1 may be two-stage desalting (salt removal). Moreover, in some examples, the desalter 118 can be two or more desalter vessels in series.

In the illustrated example, a single desalter 118 vessel is depicted. Water 142 having salt discharges from the desalter 118 and may be recycled to the dehydrator 126. Wash water 116 (e.g., fresh water) may be added to the desalter 118 vessel to facilitate removal of salt from the crude oil 140. Wash water 116 may be supplied to the desalter 118 to promote the separation generated by the electrostatic field in the desalter 118 vessel. The wash water 116 may be injected into the dehydrated crude oil 140 entering the desalter 118 to meet the salt content specification of the produced crude (export crude oil 104). The water 116 added may be low in salt concentration relative to the salt concentration of water (e.g., emulsified water) in the crude oil 140. Fresh wash water (as opposed, for example, to recycle water having more salt) may be utilized in the desalting process to increase the amount of salt rinsed from the crude oil 140. Wash water 116 salinity can range, for example, from between about 100 parts per million (ppm) to about 12,000 ppm. Again, wash water 116 may be more effective if the salinity level is low. In comparison, formation water salinity produced with crude oil can reach as high as about 270,000 ppm of salt or more.

The flowrate of the wash water 116 may be controlled via the flow control valve 114 as depicted. The valve opening (e.g., percent open) of the flow control valve may be adjusted by a flow controller (FC) to maintain flowrate of the wash water 116 per a flowrate set point of the flow controller for the control valve 114. The set point for the control valve 114 may be manually set locally or manually entered into the control system 112. On the other hand, the specifying of the flowrate of the wash water 116 may be automated. In particular, the set point for the control valve 114 may be specified by the control system 112 based on feedback from online analyzer instruments and meters in the GOSP 100. For example, the control system 112 may determine and specify the set point for the control valve 114 based in part on feedback from the online analyzer instruments 106, 108, 110.

In addition to (or in lieu of) the control valve 114, flowrate of the wash water 116 may be controlled via the speed of the pump supplying the wash water 116. The pump may be, for example, a positive displacement pump or a centrifugal pump. The speed of the pump may be manually set. In embodiments, the control valve 114 may determine and specify the speed of the pump to give the desired flowrate of wash water 116. The desired flow rate may be control-system 112 specified based at least (based in part) on measurements by the analyzer instruments 106, 108, 110. To give the desired flowrate of wash water 116, the speed of the pump may be set, for example, by adjusting the pump stroke (e.g., the number of strokes per time, the number of stroke cycles per time, the length of a stroke, etc.). In some implementations, the adjustment of the pump stroke may be manual (local) or remotely adjusted by the control system 112 to give the flowrate wash water 116 specified by the control system 112.

As in the upstream dehydrator 126, electrostatic coalescence may be employed in the desalter 118 vessel. Electrostatic coalescence may remove water emulsion from the crude oil 140. Operating conditions in the desalter 118 may be, for example, include a temperature in a range of 70° F. to 160° F. and an operating pressure at least 25 psig above vapor pressure of the crude oil 140. The wash water 116 may increase the water droplet concentration to enhance rupturing of the protective coating surrounding the brine and promote coalescence to form larger and more easily separated droplets to meet the crude salt content specification. Both the flowrate and quality (salinity) of wash water 116 may affect the crude desalting process. The desalter 118 may reduce the salt content of crude oil 140, for example, to less than 10 pounds of salt per thousand barrels (PTB) of oil.

The crude oil that discharges from the desalter 118 may be the export crude oil 104. The desalter 118 may discharge the export crude oil 104 for distribution including to storage and transportation, and for further processing such as in a petroleum refinery. The export crude oil 104 may be labeled as processed crude oil, product crude oil, stabilized crude oil, and so forth. The salt content of the export crude oil 104 may be monitored manually by periodically determining the salt content through laboratory analysis (e.g., once per 8-hour shift). The salt content of the export crude oil 104 may be monitored by determining the salt content based on calculating a salt mass balance (e.g., in real time) in the GOSP 100 utilizing online data for streams in the GOSP 100.

Specifications for the export crude oil 104 may include, for example: (1) salt content less than 10 PTB; (2) basic sediment and water (BS&W) content less than 0.2 volume percent (vol %) of the crude oil; (3) hydrogen sulfide ($H_2S$) content less than 70 ppm by weight (ppmw); and (4) maximum true vapor pressure (TVP) (per ASTM D 2879) less than 13 pounds per square inch absolute (psia) at storage temperature. The BS&W is generally measured from a liquid sample of the crude oil. The BS&W includes water, sediment, and emulsion. The BS&W is typically measured as a volume percentage of the crude oil. The BS&W specification may be less than 0.5 vol % for Heavy crude oil and less than 0.2 vol % for other crude oils.

In some examples, the desalter 118 may discharge the export crude oil 104 via a conduit to a stabilizer distillation column (not shown) that separates and removes light ends or light components (volatile components such as C1-C4 hydrocarbons) as gas from the export crude oil 104. These light components may discharge as an overhead stream from the stabilizer distillation column. This removal of the light components reduces vapor pressure of the export crude oil 104 to give a desired vapor pressure of the export crude oil 104 as stabilized crude oil. The associated specification of the export crude oil 104 may be, for example, Reid vapor pressure (RVP) or true vapor pressure (TVP), or both. The term "stabilized" may refer to the crude oil having a lower vapor pressure and thus being less volatile to facilitate tank storage and pipeline transport. The stabilization may be, for example, to lower the vapor pressure of the crude oil to at least 13 pounds per square inch (psi) below atmospheric pressure so that vapor will generally not flash under atmospheric conditions. The stabilizer distillation column may remove $H_2S$ from the export crude oil 104 to sweeten the crude oil. The $H_2S$ may discharge in the overhead stream in the light components. The terms "sweet" crude oil or to "sweeten" crude oil refers to lower $H_2S$ content in the crude oil. In the stabilizer distillation column, any $H_2S$ gas dissolved in the export crude oil 104 is removed to meet crude-oil specification of $H_2S$ content, for example, less than 60 ppm, or in a range of 10 ppm to 70 ppm. If a stabilizer distillation column is employed, the stabilized export crude oil 104 may be discharged as the bottom streams from the stabilizer distillation column and pumped via the column bottoms pump to storage or distribution.

The GOSP 100 may include a control system 112 that facilitates or directs operation of the GOSP 100. For instance, the control system 112 may direct control of the supply or discharge of flow streams (including flowrate) and associated control valves, control of operating temperatures and operating pressures, and so on. The control system 112 (or associated computer system) may perform salt mass-balance calculations of the GOSP 100 to determine (monitor) the salt content in the export crude oil 104. The determination may be based on on-line analysis upstream (internal) in the GOSP 100. The salt content in the export crude oil 104 may be determined in real time (or substantially real time) without online analysis of the export crude oil 104 itself.

In some implementations, the control system 112 may calculate or otherwise determine set points of control devices. For instance, the control system 112 may specify the set point of the flow control valve 114 (or specify number of strokes per time for a wash-water supply pump) on the wash water 116 supply to the desalter 118.

The control system 112 may include a processor and memory storing code (e.g., logic, instructions, etc.) executed by the processor to perform calculations and direct operations of the GOSP 100. The processor (hardware processor) may be one or more processors and each processor may have one or more cores. The processor(s) may include a microprocessor, central processing unit (CPU), graphic processing unit (GPU), controller card, circuit board, or other circuitry. The memory may include volatile memory (for example, cache or random access memory), nonvolatile memory (for example, hard drive, solid-state drive, or read-only memory), and firmware. The control system 112 may include a desktop computer, laptop computer, computer server, control panels, programmable logic controller (PLC), distributed computing system (DSC), controllers, actuators, or control cards.

The control system 112 may be communicatively coupled to a remote computing system that performs calculations and provides direction. The control system 112 may receive user input or remote-computer input that specifies the set points of control devices or other control components in the GOSP 100. The control system 112 may employ local control panels distributed in the GOSP 100. Certain implementations may include a control room that can be a center of activity, facilitating monitoring and control of the GOSP 100 process or facility. The control room may contain a human machine interface (HMI), which is a computer, for example, that runs specialized software to provide a user-interface for the control system. The HMI may vary by vendor and present the user with a graphical version of the remote process. There may be multiple HMI consoles or workstations, with varying degrees of access to data.

As indicated, after dewatering the crude oil 102 emulsion in the phase separators HPPT 122 and LPPT 128 (and/or LPDT), the crude oil 138 stream undergoes a stage of desalting at each of the dehydrator 126 and the desalter 118. If not desalted, the small brine droplets contained in the crude oil 138 stream leaving the LPPT 128 (or LPDT) may corrode pipes and storage tanks. In addition to the corrosion of metallic equipment, high concentration of salts within these brine droplets could foul or plug trays in distillation columns, heat-exchanger tubes, etc. at downstream refineries. Therefore, the level of salt in the export crude oil 104 is regulated and controlled, for example, to under 10 pounds salt (as sodium chloride equivalent) per 1,000 barrels crude oil (10 lbm salt/1000 bbl crude oil or PTB) for transportation and storage, and to under 1 lbm salt/bbl crude oil for petroleum refineries. One pound salt per thousand barrels is equivalent to 28.5 gram of salt/m3 (or ppmw). In some examples, the water volume fraction (level of residual brine) may be regulated and controlled to maximum 0.5 volume percent (vol %) for heavy crude oils (e.g., Heavy Arabian crude oil) and maximum 0.2 vol % for other crude oils (e.g., Arabian crude oils). The water volume fraction may be regulated and controlled to other product-specification values (vol %) for water volume fraction as applicable for other types or grades of crude oil, or may be customer dependent.

As indicated, aspects of the present disclosure may provide: (1) real-time, automated wash-water 116 flowrate to the desalter 118 for control of salt content in the export crude oil 104; and (2) real-time monitoring (via calculation) of the salt content in the export crude oil 104 that exits the desalter 118.

Figure 2:
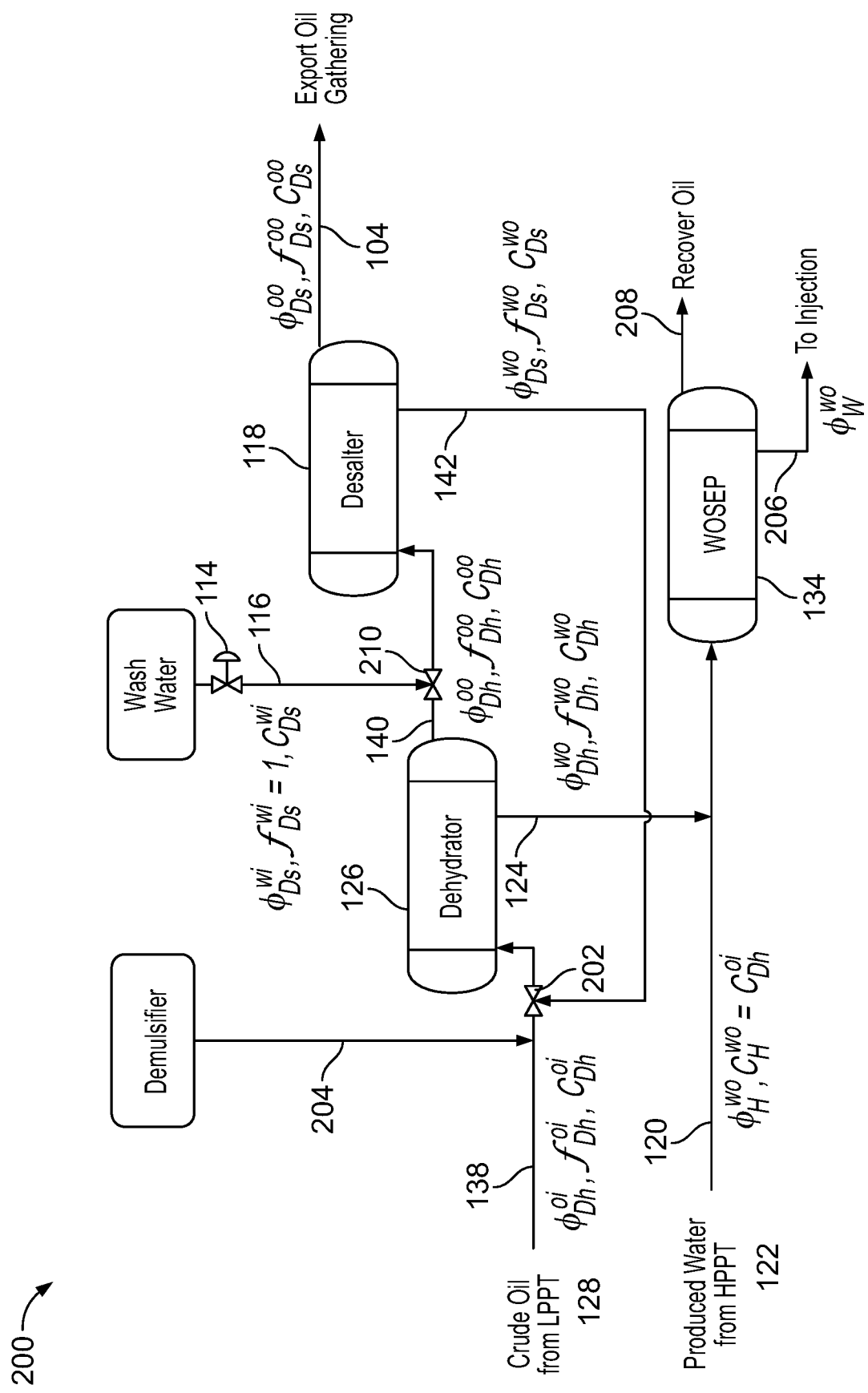
FIG. 2 is a flow diagram of the two-stage desalting of the GOSP of FIG. 1.

FIG. 2 is the two-stage desalting 200 of the GOSP 100 of FIG. 1. The two-stage desalting process includes water wash recycling. Variables of the salt mass balance(s) described below are depicted as associated with streams in FIG. 2. The two-stage desalting includes the dehydrator 126 and the desalter 118. The export crude oil 104 is discharged from the desalter 118. The dehydrator 126 receives the crude oil 138 from the LPPT 128 and recycle water 142 from the desalter 118. The recycle water 142 may be introduced into the conduit conveying the crude oil 138, such as at a mixing component 202 (e.g., mixing pipe tee, mixing valve, etc.) along the conduit. A static mixer may be installed in-line in the conduit.

A demulsifier 204 may be added to the crude oil 138 (e.g., an oil-water emulsion) to facilitate breaking of the crude oil emulsion into oil and water phases. Moreover, the demulsifier 204 may neutralize the stabilizing effect of any emulsifying agents employed in the upstream production of the crude oil. The emulsifying agents may be present at the oil-water interface, hindering this coalescence process. The demulsifier 204 may be a surface-active compound that migrates to the oil-water interface, ruptures or weakens the rigid film, and enhances water droplet coalescence. Chemical components of the demulsifier 204 may include solvents (carrier), surface-active ingredients, and flocculants. The solvents may be, for example, benzene, toluene, xylene, short-chain alcohols, and heavy aromatic naphtha. The demulsification (breaking of the emulsion) in the two-stage desalting system 200 may generally include the separation of the emulsion into its component phases and involve flocculation (aggregation, agglomeration, or coagulation) and coalescence, and the like.

As discussed with respect to FIG. 1, the produced water 120 from the HPPT 122 and the oily water 124 (e.g., less than 1 vol % oil) from the dehydrator 126 are sent to the WOSEP 134. Separated water 206 may discharge from the WOSEP 134 vessel, such as for injection. Separated crude oil 208 may discharge from the WOSEP 134 vessel for recovery. The water 206 and crude oil 208 streams may discharge from the GOSP 100 facility to offsite.

As also discussed with respect to FIG. 1, the wash water 116 is injected between the dehydrator 126 and the desalter 118. The wash water 116 contacts the dispersed brine droplets in the crude oil 140. The wash water 116 may be added to the conduit conveying the crude oil 140, such as at a mixing component 210 along the conduit. The mixing component 210 may be, for instance, a mixing pipe tee, mixing valve (e.g., double-ported globe valve), and so forth. A static mixer may be disposed in-line in the conduit. The wash water 116 is injected into and mixed with the crude oil 140 to facilitate reduction of the average salinity of the overall water and reduction of the distance between water droplets to enhance oil-water separation. As mentioned, water 142 from the desalter 118 is recycled and injected at the inlet of the dehydrator 126.

A mass balance of the salt may be performed on the dehydrator (Eq. 1) and the desalter (Eq. 2), as follows:

$$C_{Dh}^{oi} \cdot \phi_{Dh}^{oi} \cdot f_{Dh}^{oi} + C_{Ds}^{wo} \cdot \phi_{Ds}^{wo} \cdot f_{Ds}^{wo} = C_{Dh}^{oo} \cdot \phi_{Dh}^{oo} \cdot f_{Dh}^{oo} \cdot C_{Dh}^{wo} \cdot \phi_{Dh}^{wo} \cdot f_{Dh}^{wo} \quad \text{Eq. 1)}$$

$$C_{Ds}^{oo} \cdot \phi_{Ds}^{oo} \cdot f_{Ds}^{oo} + C_{Ds}^{wo} \cdot \phi_{Ds}^{wo} \cdot f_{Ds}^{wo} = C_{Dh}^{oo} \cdot \phi_{Dh}^{oo} \cdot f_{Dh}^{oo} + C_{Ds}^{wi} \cdot \phi_{Ds}^{wi} \cdot f_{Ds}^{wi} \quad \text{(Eq. 2)}$$

Where C is the salt mass concentration in grams per cubic meter (g/m³), ϕ is the flowrate, f is the volume fraction of water. Dh and Ds represent streams coming from or going to the dehydrator or desalter, respectively. The nature and direction of the stream are defined using wi and wo for water streams at the inlet, or outlet, respectively. Similarly, of and oo are used to indicate oil streams at the inlet or outlet, respectively.

The salt mass concentration C is the mass concentration of salt in the water (brine) in the given stream. The units may be grams salt per m³ of water. For a crude oil stream, C is the salt mass concentration in the water (e.g., brine droplets) in the crude oil.

For the mass balance, the salt concentration may be Na concentration or NaCl concentration. Therefore, while the salt in the process may include salt in addition to NaCl, the salt mass balance can have a Na or NaCl basis for the salt concentration.

In the mass balance (as discussed below), the salt content ($C_{Ds}^{oo} \cdot f_{Ds}^{oo}$) in the export crude oil 104 may be input or calculated. The salt content ($C_{Ds}^{oo} \cdot f_{Ds}^{oo}$) may be calculated to monitor (as calculated) the salt content in the export crude oil 104 in real time. The salt content ($C_{Ds}^{oo} \cdot f_{Ds}^{oo}$) may be input into the mass balance to determine (calculate) a wash water 116 flowrate $\phi_{Ds}^{wi}$ to specify as a set point to the flow control valve 114 or other control component. The salt content input (and water volume fraction input) to the mass balance may be based on a product specification of the export crude oil 104.

The analytical subtraction of the above two equations (Equation 1 minus Equation 2) gives the following expression:

$$C_{Dh}^{oi} \cdot \phi_{Dh}^{oi} \cdot f_{Dh}^{oi} - C_{Ds}^{oo} \cdot \phi_{Ds}^{oo} \cdot f_{Ds}^{oo} = C_{Dh}^{wo} \cdot \phi_{Dh}^{wo} \cdot f_{Dh}^{wo} - C_{Ds}^{wi} \cdot \phi_{Ds}^{wi} \cdot f_{Ds}^{wi} \quad \text{(Eq. 3)}$$

The volume fraction $f_{Ds}^{wi}$ is equal to 1 because there is little or no oil in the wash water. Discussed are how to determine parameters ($X_{Dh}^{oi}$) of the oil stream 138 that enters the dehydrator 126. The salt concentration $C_{Dh}^{oi}$ of the brine droplets entering the dehydrator 126 is the same or similar ($C_H^{wo} = C_{Dh}^{oi}$) as that of the produced water 120 coming from the HPPT 122. To measure the brine flowrate ($f_{Dh}^{oi} \cdot \phi_{Dh}^{oi}$), the mass balance of brine on the production facility is expressed as follows:

$$\phi_{Dh}^{oi} \cdot f_{Dh}^{oi} = \phi_W^{wo} - \phi_H^{wo} - \phi_{Ds}^{wi}$$

with $\phi_{Dh}^{oi} \cdot f_{Dh}^{oi} = \phi_E^{wi} - \phi_H^{wo}$ and $\phi_E^{wi} = \phi_W^{wo} - \phi_{Ds}^{wi}$ (Eq. 4)

Where $\phi_E^{wi}$ is the flowrate of the water in the emulsion (crude oil 102) entering the GOSP production facility, $\phi_H^{wo}$ is the water flowrate existing the HPPT and $\phi_W^{wo}$ is the water flowrate exiting the WOSEP 134, e.g., exiting the GOSP 100 production facility. The brine flowrate term of equation (Eq. 4) is replaced in equation (Eq. 3) to give the following:

$$\phi_{Ds}^{wi}(C_H^{wo} - C_{Ds}^{wi}) = C_H^{wo}(\phi_W^{wo} - \phi_H^{wo}) + C_{Ds}^{oo} \cdot \phi_{Ds}^{oo} \cdot f_{Ds}^{oo} - C_{Dh}^{wo} \cdot \phi_{Dh}^{wo} \cdot f_{Dh}^{wo} \quad \text{(Eq. 5)}$$

From the above equation (Eq. 5), the wash water flowrate can be isolated utilizing measurable parameters:

$$\phi_{Ds}^{wi} = \frac{1}{(C_H^{wo} - C_{Ds}^{wi})} \left[ C_H^{wo}(\phi_W^{wo} - \phi_H^{wo}) + C_{Ds}^{oo} \cdot \phi_{Ds}^{oo} \cdot f_{Ds}^{oo} - C_{Dh}^{fo} \cdot \phi_{Dh}^{fo} \cdot f_{Dh}^{wo} \right] \quad \text{(Eq. 6)}$$

Where the salt concentration $C_{Ds}^{oo}$ of the export crude oil 104 may be input in accordance with product specification of the export crude oil 104. For example, the salt concentration $C_{Ds}^{oo}$ may be input at 10 lbm/1000 bbl (28.5 g/m³) for transportation. Similarly, in examples, the water volume fraction $f_{Ds}^{oo}$ may be input at 0.2 vol %, except for Heavy Arabian oil (0.5 vol %). The given specification value for salt concentration and water volume fraction are generally a maximum value and thus to meet specification, the actual value in the crude oil 104 must be at or less than the specification value.

Utilizing Equation 6, based on a specified salt content of the export crude oil 104, the water wash 116 flowrate $\phi_{Ds}^{wi}$ can be calculated and directed as a set point for the flow control valve 114. The specified salt content is analogous to the salt concentration $C_{Ds}^{oo}$ in the water in the export crude oil 104 multiplied by the volume fraction of water $f_{Ds}^{oo}$ in the export crude oil 104 per an export crude oil 104 specification. The volume fraction of water of the export crude oil 104 may be the brine residual (water having salt) in the crude oil 104.

The salt content ($C_{Ds}^{oo} \cdot f_{Ds}^{oo}$) in the export crude oil 104 as a parameter in the mass balance can be extracted from equation (Eq. 5) using measurable parameters:

$$G = C_{Ds}^{oo} \cdot f_{Ds}^{oo} = \frac{1}{\phi_{Ds}^{oo}} \left[ C_H^{wo}(\phi_W^{wo} - \phi_H^{wo}) - \phi_{Ds}^{wi}(C_H^{wo} - C_{Ds}^{wi}) - C_{Dh}^{wo} \cdot \phi_{Dh}^{wo} \cdot f_{Dh}^{wo} \right] \quad \text{(Eq. 7)}$$

Figure 3:
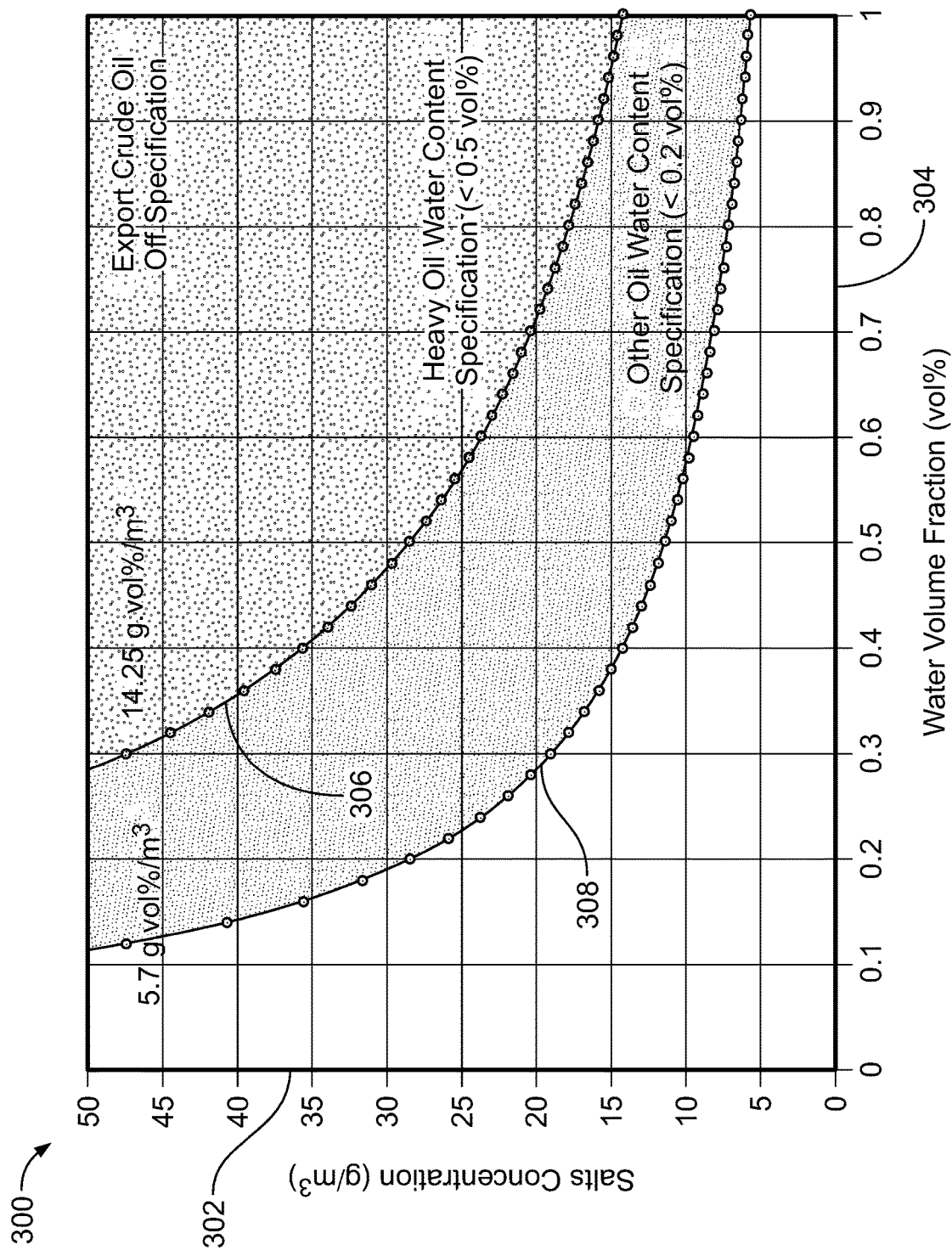
FIG. 3 is a plot of salt concentration in crude oil versus water volume fraction 304 in crude oil.

This factor G may represent salt content and can be utilized to determine when the crude oil is in specification for transport (see, e.g., FIG. 3). For the Heavy Arabian oil, the specification at maximum 0.5 vol % water (or brine residual) requires a G factor below 14.25 g·vol %/m³. For other oil having a specification, for example, at maximum 0.2 vol % water requires a G factor below 5.7 g·vol %/m³.

FIG. 3 is a plot 300 of salt concentration 302 (g/m³) in crude oil versus water volume fraction 304 (vol %) in crude oil. The curve 306 is for G equal to 14.25 g·vol %/m³. The curve 308 is G equal to 5.2 g·vol %/m³. Graphically, the crude oil which is on-specification is represented by the zone below the curve. If the value of the G factor is lower than the specification (e.g., 14.25 g·vol %/m³ for Heavy oil and 5.7 g·vol %/m³ for other oils), the oil will meet the salt content specification for the export crude oil. Again, the salt content in the export crude oil 104 may be the salt concentration in the water in the export crude oil 104 multiplied by the volume fraction of water in the export crude oil 104.

In summary, Eq. 6 can be employed in the control of the wash water 116 flowrate to give the desired salt content in the export crude oil 104. The desired salt content entered into Eq. 6 can be at or less than the product-specification value for salt content of the export crude oil 104. Eq. 7 can be employed to calculate (and thus monitor) the actual salt content in the export crude oil 104.

With respect to Eq. 6, embodiments may provide for real-time automated specifying of the wash-water 116 flowrate (e.g., in mass per time or volume per time) in the control of the crude-oil desalting in the GOSP 100. From Eq. 6, the flowrate value to specify for the set point of the wash-water flow control valve 114 can be determined. For example, this value as the value of the parameter $\phi_{Ds}^{wi}$ to specify for the set point of the control valve 114 can be determined by measuring four flowrates ($\phi_W^{wo}, \phi_H^{wo}, \phi_{Ds}^{oo}, \phi_{Dh}^{wo}$) three salinity (salt) concentrations ($C_H^{wo}, C_{Ds}^{wi}, C_{Dh}^{wo}$), and one volume fraction of water ($f_{Dh}^{wo}$ or 1-volume fraction of oil).

Figure 4:
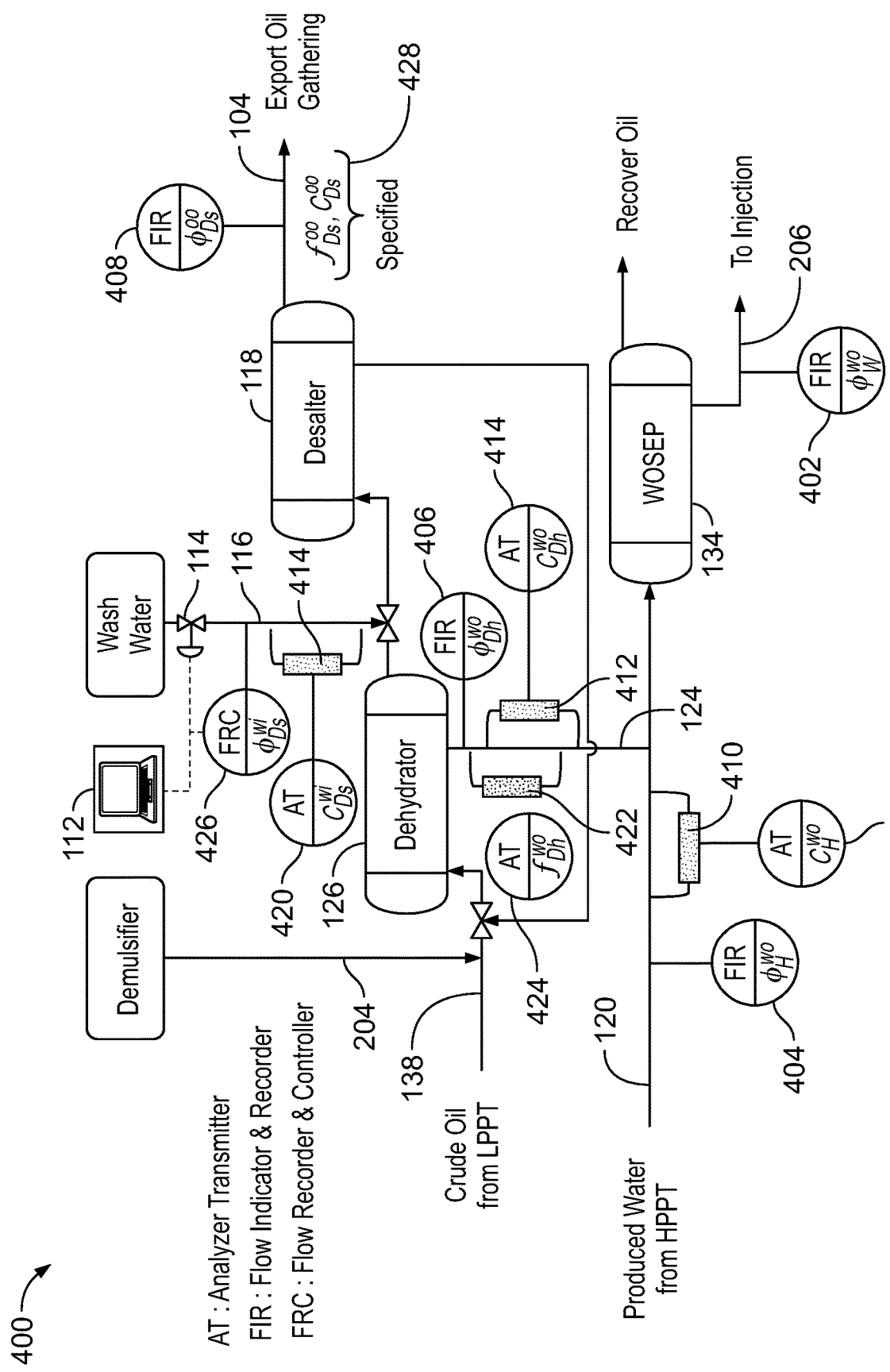
FIG. 4 is a flow diagram of the two-stage desalting as automated to designate the wash water flowrate.

FIG. 4 is two-stage desalting 400 that is the two-stage desalting 200 (FIG. 2) as automated to designate the wash water 116 flowrate. FIG. 4 depicts online instrument meters (e.g., including analyzers) and associated transmitters utilized to automate specifying the wash water 116 flowrate in real time. In general, the meters for measuring a property of the process fluid may include a sensor or sensing portion that interfaces with the process fluid and an instrument transmitter that interfaces with the control system 112 or other computing system. Moreover, some of the analyzer instruments may be an analyzer instrument system having a sampling system and the sensing portion. For example, an online nuclear magnetic resonance (NMR) spectroscope system may include a sampling system and an NMR spectroscope, as well as an analyzer transmitter (AT).

The flow meters 402, 404, 406 for $\phi_W^{wo}, \phi_H^{wo}, \phi_{Dh}^{wo}$, respectively, may be vortex flowmeters, swirl flowmeters or electromagnetic flowmeters. These meter types are generally not affected by density changes, corrosion, or solid/oil droplets contamination and deposition. For $\phi_{Ds}^{oo}$, the flow meter 408 may be a vortex flowmeter, swirl flowmeter, differential pressure flowmeter (or venture flume), ultrasonic flowmeter, or mass meter (e.g., Coriolis mass flowmeter). A respective flow indicator (FI) or flow indicator recorder (FIR) may be associated with each flow meter 402, 404, 406, 408 and indicate the measured flowrate (values) to the control system 112.

The salt meters 410, 412 for $C_H^{wo}, C_{Dh}^{wo}$, respectively, may each employ $^{23}$Sodium ($^{23}$Na) NMR spectroscopy (as an online $^{23}$Na NMR spectrometer) because $^{23}$Na NMR spectroscopy is generally not affected by ionic and polar water-soluble organic species, or by oil droplets contamination/deposition. With respect to the salt meter 414 for $C_{Ds}^{wi}$, the salinity concentration of the wash water 116 can be measured utilizing a refractometer, density meter by sound velocity measurement, contact electrical conductivity meter, toroidal/inductive electrical conductivity meter, gamma densitometer, or a $^{23}$Na NMR spectrometer (spectroscope). Each salt meter 410, 412, 414 may have an associated analyzer transmitter (AT) 416, 418, 420 to transmit a signal indicative of the measured salt concentration to the control system 112.

The salt concentration $C_{Dh}^{wo}$ of the oily water 124 discharged by the dehydrator 126 can also be determined by measuring the salt concentration and the flowrate of the oily water 206 discharged by the WOSEP 134 and subtracting them to the salt concentration and the flowrate of the water 120 discharged by the HPPT 122, as per the following equation $$C_{Dh}^{wo} = \frac{1}{f_{Dh}^{wo}\phi_{Dh}^{wo}}(f_W^{wo}\phi_W^{wo}C_W^{wo} - f_H^{wo}\phi_H^{wo}C_H^{wo}) \text{ with } f_H^{wo} \approx 1.$$

Similar mathematical operation can be undertaken for the salt concentration $C_H^{wo}$ of the water 120 discharged by the HPPT 122.

The meter 422 to measure volume fraction of water can be a density meter or other type of meter. An AT 424 may indicate the measured volume fraction to the control system 112. The AT 424 may transmit to the control system 112 a signal indicative of the vol % of water in the oily water 124 as measured by the meter 422.

For $C_H^{wo}$, a density meter may be employed but extensive calibration might be implemented due to this aqueous stream being a complex mixture of dissolved gases, dissolved organics, salts, and water. For $C_H^{wo}$, a conductivity meter may be employed but can be inaccurate in implementations because the conductivity is not linear within a wide range of salt concentration. For $C_{Dh}^{wo}$, a density meter may be utilized but significant error may be realized on the density measurement due to the variation of relatively large amount (roughly 1-5 vol %) of oil droplets in this water stream. For $C_{Dh}^{wo}$, toroidal/inductive electrical conductivity meter may be utilized but excessive maintenance of this conductivity probe may be experienced in examples because the water 124 from the dehydrator 126 may contain a relatively large number of oil droplets (approx. 1-5 vol %).

Again, FIG. 4 depicts online instrumentation that may be utilized in the automation of specifying the wash water 116 flowrate. The control system 112 may specify the set point of the flow controller (FC) or flow recorder controller (FRC) 426 for the flow control valve 114. Thus, in certain implementations, the FRC 426 may be characterized as a slave controller, e.g., slave to the control system 112 or slave to a master controller in the control system 112. This master controller in the control system 112 may perform the salt mass-balance calculations in certain examples. The FRC 426 may rely on a flow meter to determine the flowrate of the wash water 116. The flow meter may be, for example, a differential pressure meter with a flow orifice (restriction orifice) in the conduit conveying the wash water 116. In directing FRC 426, the control system 112 may utilize Eq. 6 and feedback from the depicted meters (including the online analyzers), and rely on the specified salt content 428 of the export crude oil 104 input to the control system 112 for the mass-balance calculations. The input salt content 428 may represent the product of water salt concentration and water fraction, and have units, for example, of g·vol %/m$^3$.

The measurement frequency of the meters 402, 404, 406, 408, 410, 412, 414, 422 may be, for example, at intervals less than one second, less than five seconds, less than one minute, or less than 5 minutes. Therefore, the control system 112 may determine (calculate) in real time (or substantially real time) the set point (value) to specify for the FRC 426. The control system 112 may be tuned to specify (direct) the set point of the FRC 426 in real time at a particular frequency (e.g., an interval of every second, minute, or hour). The interval designated may be beneficial for stability of the FRC 426 control loop, operational stability of the desalter 118 operation, and operational stability of the overall two-stage desalting 200 process. The particular frequency designated may also be correlative with the measurement frequency of the aforementioned meters. In summary, in one example based on the amount of salt in GOSP 100 streams as measured and calculated and on a specified value for water fraction (volume fraction) in the export crude oil 104, the control system 112 may specify a wash water 116 flow rate to maintain the salt content in the product crude oil 104 within specification.

The salt concentration or salt content in the export crude oil 104 generally cannot be reliably measured online. Therefore, based on the salt concentration in GOSP 100 streams as measured and calculated (and in certain implementations additionally based on an input value for water volume fraction in the export crude oil 104), the control system 112 may determine (calculate) the salt content in the export crude oil 104.

Figure 5:
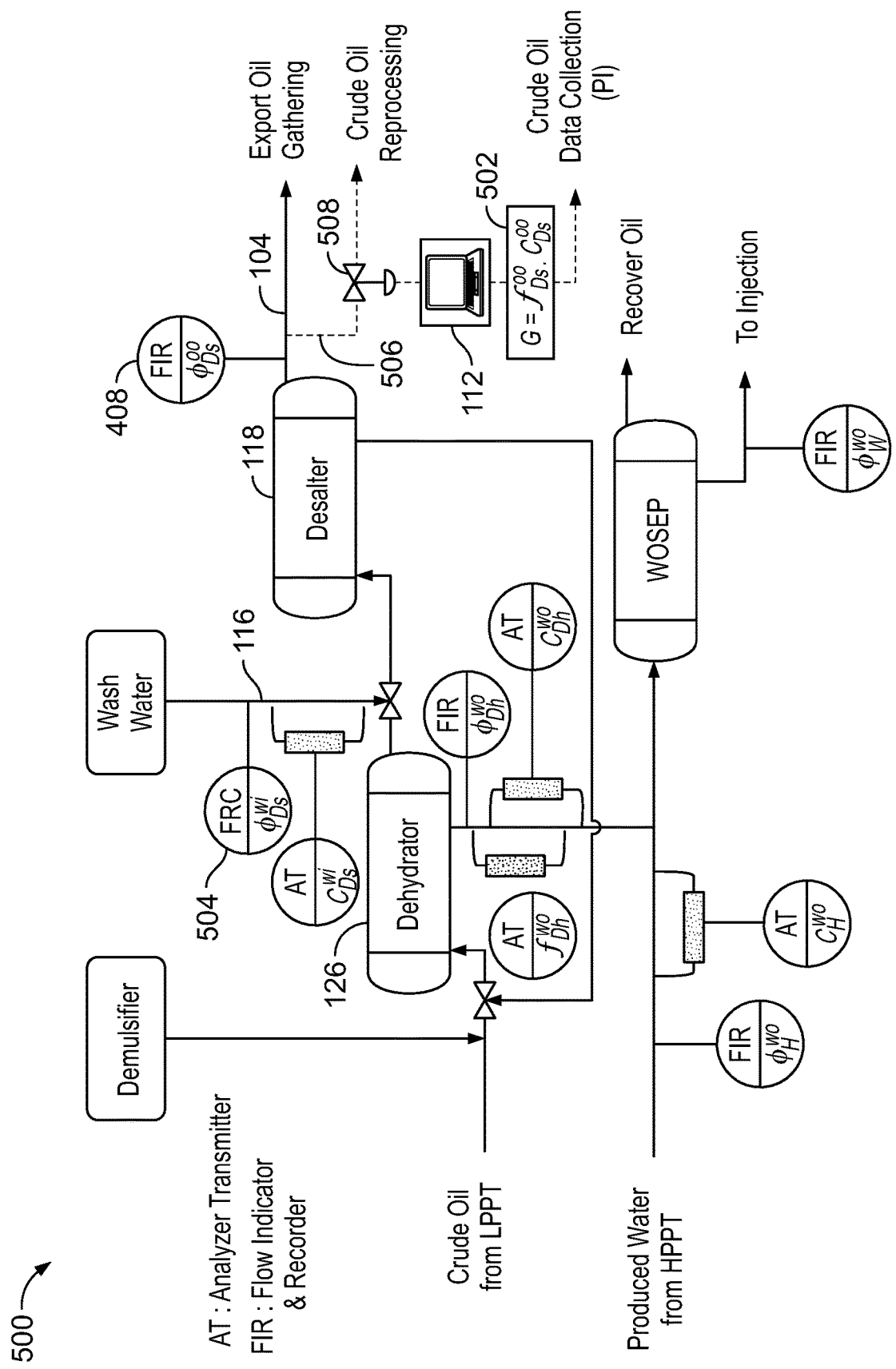
FIG. 5 is two-stage desalting as configured to determine (calculate) the actual salt content in the export crude oil.

FIG. 5 is two-stage desalting 500 that is the two-stage desalting 200, 400 (FIGS. 2 and 4) as configured to determine (calculate) the actual salt content 502 in the export crude oil 104. The calculation (e.g., by the control system 112) may be based on the aforementioned Eq. 7, the flowrate of wash water 116 as indicated by FIR 504, and feedback from the other depicted meters (including online analyzer instruments). This actual salt content 502 may be monitored via the determination or calculation of the salt content 502. This actual salt content 502 in the export crude oil 104 as determined may be compared to the product-specification salt content (e.g., designated salt content 428 of FIG. 4) for the export crude oil 104. If not in specification, the export crude oil 104 may be diverted as off-spec crude oil 506 through a conduit to crude oil reprocessing. The control system 112, in response to the calculated value of salt content 502 being out of specification, may open a control valve 508 along the conduit. The off-spec crude oil 506 may be recycled to the dehydrator 126 or the desalter 118, or to other reprocessing.

The two-stage desalting 500 may include a flow indicator (FI) or flow indicator recorder (FIR) 504 for the wash water 116. The FIR 504 may include a flow meter along the wash water 116 conduit to determine (measure) the flowrate of the wash water 116. The flow meter may be, for example, a differential pressure meter with a flow orifice (restriction orifice) in the conduit conveying the wash water 116. The indicated flow rate of the wash water 116 may be employed in the calculated salt mass balance.

While not depicted, the two-stage desalting 500 may also include the wash water 116 control valve 114 (see FIGS. 1, 2, and 4). Thus, the FIR 504 may instead be a flow controller, such as an FC, FRC, flow indicator controller (FIC), etc., associated with (tied to) the control valve 114. The set point for the flow controller for the controller valve 114 may be manually input. The operational mode (associated with FIG. 5) may rely on Eq. 7 to determine that actual salt content 502 and not rely on Eq. 6 to automatically specify the set point for the wash water 116 control valve 114.

However, the two-stage desalting 500 can be configured with the features of the two-stage desalting 400 of FIG. 4. In other words, an implementation of the two-stage desalting may be configured as a combination of FIG. 4 and FIG. 5. In that implementation, the control system 112 may receive user input to select the operational mode (automated wash water 116 rate) discussed with respect to FIG. 4 or the operational mode (calculated monitoring of salt content 502 of the export crude oil 104) discussed with respect to FIG. 5.

An embodiment is a GOSP including a first production trap (e.g., HPPT 122) to receive crude oil from a wellhead and remove gas and water from the crude oil. The first production trap has an outlet to discharge a first water stream (e.g., 120) into a first conduit. The first water stream may flow via the first conduit, for example, to a water/oil separator (e.g., WOSEP 134). A first online analyzer instrument (e.g., 108, 416) (e.g., including an online $^{23}$Na NMR spectroscope) is disposed along the first conduit to determine a first salt concentration in water in the first water stream. The GOSP includes a second production trap (e.g., LPPT 128) to receive the crude oil from the first production trap and remove gas from the crude oil. The GOSP includes a dehydrator (e.g., 126) vessel to receive the crude oil from the second production trap and remove water from the crude oil. The dehydrator vessel has an outlet to discharge a second water stream (e.g. 124) into a second conduit. The second water stream may flow via the second conduit, for example, to the water/oil separator. A second online analyzer instrument (e.g., 110, 418) (e.g., including an online a $^{23}$Na NMR spectroscope) is disposed along the second conduit to determine a second salt concentration in water in the second water stream.

In this embodiment, the GOSP has a desalter (e.g., 118) vessel to receive the crude oil from the dehydrator vessel and remove water (e.g. 142) including salt from the crude oil and discharge export crude oil (e.g., 104). The GOSP may include recycle conduit to route the water (e.g. 142) having salt (e.g., NaCl) removed from the crude oil by the desalter vessel to the dehydrator vessel. The GOSP may include a control system (e.g., 112) to determine (e.g., calculate) salt content in the export crude oil correlative with at least the first salt concentration and the second salt concentration, and with a salt concentration in wash water provided to the desalter vessel. The GOSP may include a control system (e.g., 112) to specify flowrate of wash water (e.g., 116) to the desalter vessel correlative with (based in part on) the first salt concentration, the second salt concentration, and a specified salt content (e.g., 428) of the export crude oil. The salt concentration in the wash water may be considered. In other words, the control system may specify the flowrate of wash water to the desalter vessel correlative with the first salt concentration, the second salt concentration, salt concentration in the wash water, and a specified salt content (e.g., 428) of the export crude oil. The GOSP may include a supply conduit to provide wash water to the desalter vessel, a third online analyzer instrument (e.g., 106, 420) disposed along the supply conduit to determine a third salt concentration in the wash water, and a flow control valve (e.g., 114) disposed along the supply conduit. The control system may specify flowrate of the wash water through the supply conduit via specifying a set point of the flow control valve. The specified flowrate may be correlative with or based at least on the first salt concentration, the second salt concentration, the third salt concentration, and the designated salt content of the export crude oil.

Nuclear magnetic resonance (NMR) spectroscopy is generally a non-destructive technique that can be utilized to study the chemical properties of matter, typically in the liquid or solid state. The technique relies on the magnetic resonance phenomenon, in which the interaction of atomic nuclear spins with a static magnetic field leads to the spins being distributed into discrete non-degenerate energy states. The number of energy states that result are equal to 2l+1, where l is the spin quantum number. For example, spins in isotopes with l=±½ (like protium or $^1$H) are distributed amongst 2 energy levels while those with l=±3/2 (such as sodium-23 or $^{23}$Na) split into 4 energy levels. Chemical information about the atoms can be obtained by perturbing the spin population distribution through the application of external electromagnetic fields and acquiring the resulting signal.

A wide range of isotopes possess the property of spin, such as $^1$H, $^{13}$C, $^{31}$P and $^{23}$Na, and thus, are susceptible to NMR spectroscopic measurements. To perform measurements of these nuclei via modern NMR spectrometers, a sample is placed in a magnet to be polarized. These magnets are typically permanent magnets with a relatively low magnetic field strength (e.g., low-field magnets) or superconducting magnets composed of wires arranged in a coil that can be fabricated to achieve high magnetic field strengths (e.g., high-field magnets). The strength of the magnet is typically reported in Tesla (T) or, among NMR spectroscopists, in the Larmor frequency (MHz) of $^1$H. Generally speaking, the Larmor frequency of a nucleus scales directly with its magnetogyric ratio and the magnetic field strength. The sample is supported inside the magnet in an attachment called a probe. The probe is designed to irradiate the sample with precisely timed radiofrequency pulses, which cause the spins to precess at the Larmor frequency of the nucleus. The precession produces a current in the receiver coil housed in the probe and this signal is acquired to ultimately record a free-induction decay (FID), which charts the intensity of the signal over time. The FID is Fourier transformed into a spectrum with intensity on the y-axis and "chemical shift" on the x-axis. The chemical shift scale is field-strength independent and may be reported in units of "ppm". The electron environments around the nuclei of different chemical groups dictate their position on the chemical shift scale, allowing NMR to be a beneficial technique for chemical investigations. The detailed discussion herein regarding aspects of NMR spectroscopy and application of NMR spectroscopy is not intended to limit aspects of the present techniques.

A feature of NMR spectroscopy is the relatively slow relaxation of spins back to their equilibrium population distribution that occurs after an application of a radiofrequency pulse. There are at least two relaxation processes in NMR spectroscopy, namely longitudinal (or $T_1$) relaxation and transverse (or $T_2$) relaxation. $T_1$ relaxation refers to the loss of energy to the molecular lattice. $T_1$ is typically measured utilizing the inversion recovery experiment, where a series of data points are recorded at different time intervals after an inversion pulse (180° pulse), and is then read by a hard pulse (90° pulse) at pre-determined intervals. Fitting these data to an exponential leads to the determination of the $T_1$ constant. On the other hand, $T_2$ relaxation relates to the loss of energy to neighboring spins. $T_2$ relaxation is typically measured utilizing the Carr-Purcell-Meiboom-Gill (CPMG) experiment, where after a 90° pulse, a loop containing a set time delay ($\tau$), a 180° pulse, and another $\tau$ delay is repeated for a pre-determined number of times. The decay that results is fit to an exponential decay to determine the $T_2$ constant.

$T_1$ and $T_2$ constants provide information that can be employed for a host of applications. For instance, magnetic resonance imaging (MRI) employs $T_1$ and $T_2$ weighted images of $^1$H to make medical diagnoses, while NMR logging is a tool amongst petrophysicists to determine properties of reservoir rocks. Depending on the desired nucleus, properties of solutions such as concentration and viscosity can also be determined. As an example, for $^{23}$Na (100% natural abundance with a relatively high sensitivity), $T_2$ is found to scale with concentration as shown in FIG. 6.

Figure 6:
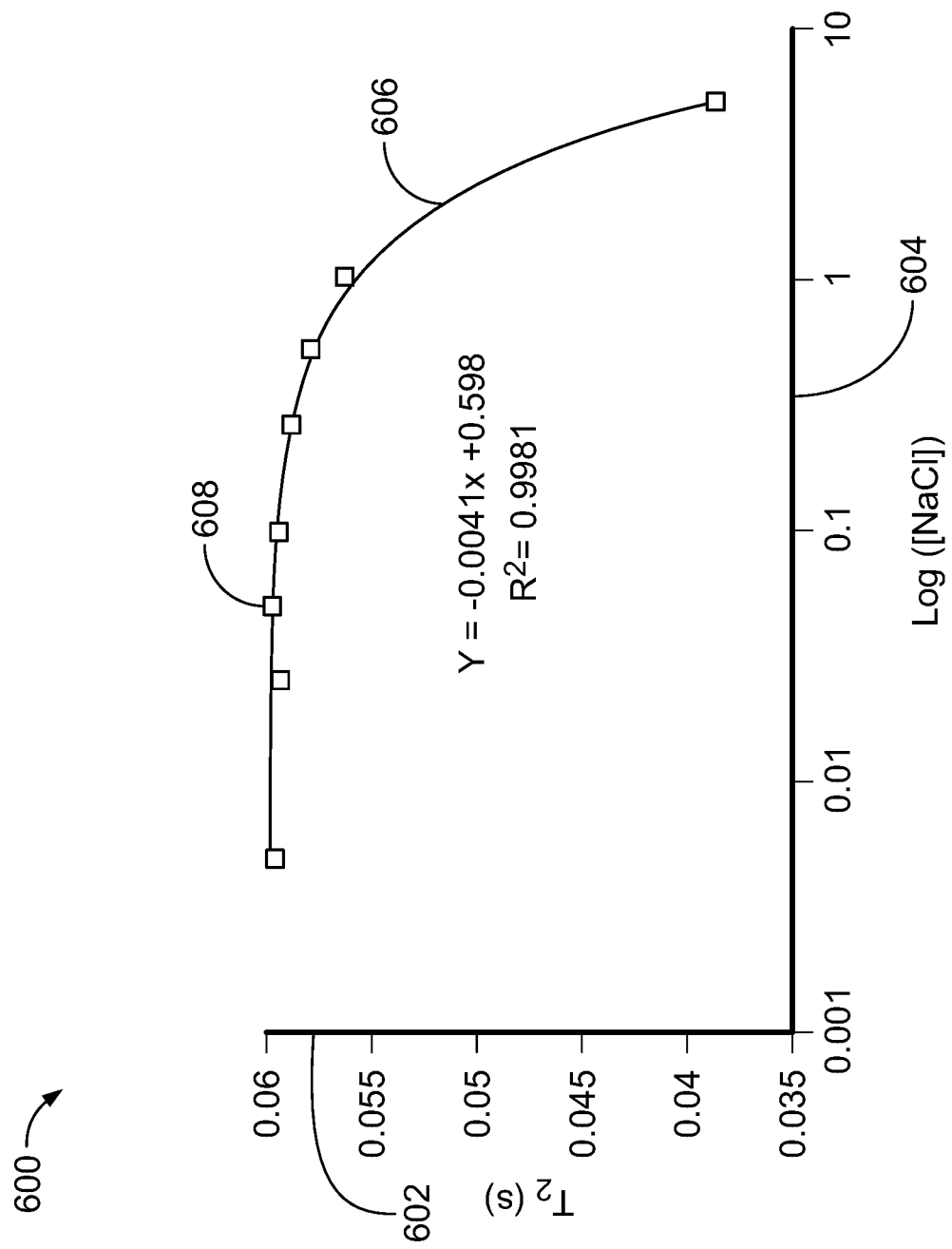
FIG. 6 is a plot of the $T_2$ relaxation constant versus the logarithmic of brine concentration.

FIG. 6 is a plot 600 of the $T_2$ relaxation constant 602 (seconds) versus the logarithmic 604 of brine concentration (weight fraction NaCl). The plot 600 indicates the linear relationship between $^{23}$Na $T_2$ (sec) constant and concentration of brine (NaCl) as measured on a high-field NMR spectrometer. The curve 606 is a fitted curve through eight data points 608 (log 604, $T_2$ 602). The curve 606 indicates the relationship between $T_2$ and NaCl concentration in brine. For $T_2$ 602 versus the log 604 of brine concentration, the coefficient of determination ($R^2$) of the curve 606 is 0.9981.

Low-field $^{23}$Na NMR spectroscopy for measuring sodium concentration may be applied. $^{23}$Na is a relatively sensitive nucleus in NMR terms (relative to $^1$H, the sensitivity is approximately 10% of $^1$H). This means that NMR may be utilized in implementations to quantify relatively low concentrations of $^{23}$Na within process fluids. The measurement employment is to quantify $M_0$, the $^{23}$Na magnetization, which is directly proportional to the number of NMR active ($^{23}$Na) nuclei. The objective may be to make this measurement independent of other parameters (e.g., all other parameters), including temperature, flow conditions and fluid constituents, and their effects on the NMR relaxation parameters $T_1$ and $T_2$. Although not necessary to measure $T_1$ and $T_2$ to quantify $M_0$, the $T_1$ and $T_2$ values and variability due to variations in the experiment conditions may affect the ability of NMR to measure $M_0$ consistently, as most NMR pulse sequences impart both $T_1$ and $T_2$ contrast to a greater or lesser degree.

For $T_1$ relaxation, the magnetization response of an inversion recovery experiment is given by equation (Eq. 8) below, where M(t) is the produced z axis magnetization at time t and $M_0$ is the equilibrium magnetization.

$$M(t) = M_0\left(1 - 2e^{\frac{-t}{T_1}}\right) \tag{Eq. 8}$$

For $T_2$ relaxation the echo amplitude of a CPMG sequence A at echo time t is given by equation (Eq. 9) below where n is the echo number, $2\tau$ is the echo spacing, $\gamma$ is the magnetogyric ratio, g is the magnetic field gradient across the sample (assumed to be uniform), and D is the sample diffusion coefficient.

$$A(t = 2n\tau) \propto M_0 \exp\left(\frac{2n\tau}{T_2} - (\gamma g)^2 \frac{2}{3} D n \tau^3\right) \tag{Eq. 9}$$

In an example of online/at-line measurements to evaluate $M_0$, Eq. 8 can be utilized to determine the time required for polarization (the time that the sample should be exposed to the static magnetic field in order to obtain its maximum signal value). Typically, M(t) is evaluated at different $\tau$ values and then the produced data fitted according to equation (Eq. 8) to obtain $T_1$. Typically, 5× $T_1$ (recovering 99.99% of the signal) may be employed as a polarization time in laboratory experiments. In low signal to noise logging experiments, 3× $T_1$ (recovering 95% of the signal) is often used. Eq. 9 gives the echo amplitude for a CPMG sequence. Note that although the CPMG sequence is commonly referred to as measuring $T_2$, the CPMG sequence also has a term dependent on diffusion (D) and magnetic field gradient/magnet inhomogeneity (g). The effect of this term can be reduced or minimized by reducing $\tau$ or g. This reduction can be relevant in NMR performed in systems with large magnet inhomogeneity, such as logging tools, where large magnetic field gradients (values of g) have significant effects on the CPMG response, or unilateral (one sided) NMR magnets, which may be relevant to process online applications.

Variation in relaxation parameters presents complexities in the attempt to quantify $M_0$. $T_1/T_2$ knowledge (as opposed to measurement) may be beneficial because if $T_1$ is unknown, the time duration for which the sample should be polarized in order to obtain the maximum value (or near maximum value) of $M_0$ may be difficult to know. If $T_1$ varies to a degree that 100% polarization is not achieved, the $M_0$ measurement will generally become dependent on the polarization time. The measurements may be performed with partial (and again consistent) polarization, but this may lead to a higher sensitivity dependence on $T_1$ compared with full (or near full) polarization and can result in a poorer signal to noise ratio (SNR) and likely a greater measurement error. $T_2$ knowledge is typically beneficial because pulse sequences such as CPMG can be potentially applied to enhance the SNR of the measurement so $M_0$ can be obtained more accurately. But, if $T_2$ varies too much, this measurement may produce varying $M_0$ results. If the $T_2$ of the sample varies, then the introduction of the $T_2$ weighting may lead to variability in the measurement consistency.

A third pulse sequence known as a free induction decay (FID) may be a basic NMR pulse sequence (e.g., the most basic NMR pulse sequence) for measuring $M_0$. In applications, the FID sequence can be employed as a sequence to measure $M_0$. The FID sequence may be relatively simple in relying, for example, on a single radio-frequency (RF) pulse followed by data acquisition. The simplicity may mean there are less variables in comparison to the CPMG sequences and therefore less potential for error, and the hardware requirements can be less demanding. In the event relaxation is dominated by $T_2$ relaxation rather than magnet inhomogeneity, the signal response may be dominated by sample $T_2$ relaxation properties. Otherwise, the event relaxation may be dominated by magnet inhomogeneity. Thus, in short $T_2$ samples such as solids, FID data generally reflects $T_2$ and in long $T_2$ samples such as liquids FID data reflects magnet inhomogeneity. The amplitude of the first few data points in an FID experiment are proportional to $M_0$. As increasing points are included in the measurement, the response becomes increasingly $T_2$ and magnet inhomogeneity weighted. This characteristic relaxation time of the FID is often referred to as $T_2^*$ (as opposed to $T_2$). Signal amplitude from the FID may be lost in the pulse dead time. This may be significant if the dead time is long and the $T_2$ of the sample is short. Signal amplitude that is lost due to $T_2$ and diffusion is generally not recoverable by CPMG sequence, but amplitude lost due to magnet inhomogeneity generally is recoverable by CPMG sequence. This means that CPMG sequences are often more accurate for producing accurate $M_0$ values in logging tools, where the effective magnet inhomogeneity (field gradient) in certain tool types is high. In this environment, FID sequences cannot be used because significant decay of the magnetization occurs during the RF pulse dead time. Reduction or minimization of the probe dead time can produce more accurate determination of $M_0$ for the FID sequence, but may lead to issues regarding the available SNR of the experiment due to the compromise in RF design.

Advantages for the CPMG sequence in the measurement of $M_0$ may include: utilization in inhomogeneous or homogenous magnets; multiple echoes to enhance SNR; and simultaneous measurement of $T_2$ allowing monitoring of sample composition (and by implication, measurement of $T_1$). Disadvantages for the CPMG sequence may include: multiple RF pulses (which places more demands on the NMR hardware); a greater number of measurement parameters (which increases possibility for errors); and the measurement and amplitude of the echoes produced is/are relatively frequency sensitive.

An advantage for the FID sequence is a simple sequence (e.g., a single RF pulse) and thus both the possibility of error and the demand on hardware (RF amplifiers and spectrometers) may be less. Consequently, the hardware can be engineered at lower cost in implementations. Advantages may for the FID sequence may include lower susceptibility to diffusion, and the measurement being relatively frequency insensitive. Disadvantages for the FID sequence may include less opportunity to enhance signal to noise than CPMG measurements, and less optimal for use in inhomogeneous magnets and systems with long probe dead times where significant signal decay may occur during the probe dead time period.

It may be possible to acquire FID and CPMG data simultaneously using a single sequence with little or no time penalty, although implementing this may make the spectrometer electronics somewhat more complex. In attempting to measure $M_0$, there are at three variables (e.g., key variables) that may contribute to $M_0$ variation. These are temperature effects, sample composition effects, and flow condition effects. Attempts should generally be made to reduce or minimize these effects, as well as compensate for their variability.

Temperature can affect the response in several ways. Firstly, temperature may affect the $M_0$ value through the Boltzmann distribution and the ultimate $M_0$ value produced at a particular magnetic field ($B_0$) strength. Secondly, temperature can impact the $M_0$ value through variation in the $T_1$ (polarization time). Thirdly, temperature can affect measurement sequences such as CPMG, both through the $T_2$ and diffusion terms, so using a CPMG sequence to obtain $M_0$ could cause inaccuracies. In order to resolve temperature issues, there are at least two strategies. One is to measure the temperature and compensate for the effects both on $T_1$ and $T_2$ and absolute $M_0$ values (derived from the Boltzmann distribution). The other strategy is to attempt to hold the temperature constant.

Sample composition effects can affect the $M_0$ response. For instance, increased concentration of a particular impurity may affect $T_1/T_2$ response causing a reduction in $T_1/T_2$ via an enhanced relaxation measurement, which may impact the $M_0$ measurement. Also, a particular impurity may affect magnet homogeneity (for example a fine suspension of iron particles) leading to changes in the signal response. These effects can be mitigated in certain implementations by monitoring changes in the $T_1/T_2$ response and compensating for them. An additional composition effect might be due to another sample constituent having similar frequency to that of the target nucleus, and being excited and therefore appearing as an additional NMR signal in the data. This signal can likely be dealt with by post processing/digital filtering techniques. There are several relatively sensitive nuclei, including $^{51}V$, which are close to $^{23}Na$ in frequency which may be problematic if present in high enough concentrations.

Flow speed may affect the amount of time that the sample is exposed to the $B_0$ field, and the amount of time the nuclei have to polarize. There are at least four strategies to address this. The first is to attempt to keep the flow constant. The second is to measure the flow speed and compensate for it. The third is to design the magnetic field profile such that the flow speed becomes irrelevant. The fourth is to modify $T_1$ such that flow speed becomes irrelevant (as $T_1$ becomes shorter, the nuclei take less and less time to polarize and therefore the time they spend in the magnetic environment). Another issue with flow speed is how flow speed affects the result of CPMG sequences. CPMG sequences may take a significant amount of time for the sequence to be performed. During this time, the excited sample could move outside the sensitive detection region of the probe, so that when long trains of RF pulses are applied, the sample may be outside the detection region when later pulses are applied. These effects can be reduced or minimized by shortening the CPMG parameters (r value and number of echoes) in the sequence or extending the detection regions.

Flow phase temporal composition heterogeneity may cause issues if the fluid comprises of varying amounts of two phases (such as air and water with dissolved $^{23}Na$). The air phase will have zero apparent sodium and therefore the sodium content in the water will be underreported. At least two solutions address this. One is to measure the amount of air present. Another is to measure the amount of the liquid present (possibly through $^1$H NMR or another technique) and use that to compensate the results. At-line applications may incorporate systems to expel air, so constant amounts of fluid are measured. Flow phase spatial heterogeneity occurs if the fluid comprises of two phases that are not evenly distributed within the pipe cross section, which may cause issues with reporting $M_0$. A first issue is that the NMR excitation (and therefore detection) response is not normally uniform over the detection region. The second is that if a phase has more contact with for example the surface of the pipe, the flow speed may be reduced due to the effects of Newtonian flow (zero velocity at contact with the pipe). Such may lead to enhanced time within the magnet and therefore enhanced polarization compared with fluid in the center of the pipe. At least four potential solutions exist to address this. One is to homogenize the flow. The second is to extend the polarization time. The third is to measure and compensate, which may be difficult. The fourth is to extend the detector region.

The choice of an at-line or online measurement system for the application may have an effect on the complexity of interpretation and possibly the system cost. At-line advantages may include potential to have a smaller pipe diameter and a smaller magnet diameter (not as large as main flow pipe), potentially control the sample temperature better, overcome polarization issues, overcome composition issues via air expulsion/appropriate pipework geometry, relatively easier to work on system (at-line sample pipe can generally be removed/replaced at will), temporal resolution can be traded for SNR in a static sample, and knowledge of fluid volume typically not required. At-line disadvantages include need for valves and moving parts in order to place the sample inside the instrument, possibility for fouling, measurement temporal resolution is reduced, and repetition time generally not shortened by sample replacement if $T_1$ is long. Online system advantages include typically no valves, moving parts, or waste, and generally include increased measurement temporal resolution and with experiment repetition time may become irrelevant if flow speed is high. Online system disadvantages may include: magnet and RF probe designed to fit existing pipe diameter (hardware more customized); existing pipework to be made NMR compatible (potentially more invasive); polarization time may be an issue for fast flowing fluids, and a system may require additional hardware to increase polarization (pre-polarizing magnets; significant lengths of NMR compliant pipework to be attached (the pipework directly in the flow stream rather than fitted on diverters and thus more difficult to fit and replace); and rely on knowledge of fluid flow rate to quantify concentration of $^{23}$Na.

From a purely NMR perspective, at-line solutions may be beneficial in terms of NMR hardware design and cost. Whether more beneficial in terms of plant engineering depends on the application. The magnet design may vary considerably depending on whether an online or at-line system is utilized. Online systems implement that the magnet fit around the plant pipework and therefore have a plant-defined diameter. Halbach magnets may be advantageous for this application from a magnet efficiency perspective, although their build difficulty can be high. More traditional pole-based magnet designs can be employed but typically less efficient. Online systems may also require pre-polarization mechanisms, although homogeneity is not necessary for the pre-polarization stage. Online measurements could also be made by unilateral (one sided) magnets, but these magnets may pose a significant amount of additional measurement complexities. For at-line applications, a wider range of magnets may be applicable as the pipework (and therefore the magnet usable gap) would not necessarily be constrained by the plant requirements for fluid flow (the plant pipe diameter). The optimization task may be to increase or maximize the magnetic field strength and allow an appropriate sample size while maintaining low system engineering costs. Pre-polarization magnets may not be necessary because the sample would generally be static in the magnet in order to polarize. Existing magnet designs can likely be adapted to at-line applications, which would reduce development costs. Magnet materials in both cases (at-line and online) may be samarium colbalt (samco), mainly due to its environmental resistance (high temperature range), frequency stability, and large attainable field strength. Achievable magnet field strength ($B_0$) with samco is somewhat less than using neodymium, but not significantly so. The RF amplifier is a significant cost component in most NMR systems. An online system running CPMG experiments may rely on higher power and expensive RF amplifiers, whereas at-line systems may rely relatively low amplifier power for RF excitation and hence significantly reducing cost. Most modern NMR spectrometers are capable of performing the pulse sequences. Some reduction in usual spectrometer capability could lead to improvement in implementation costs.

RF probe design is a consideration for this application to achieve increased or maximum sensitivity of the $^{23}$Na nucleus. The probe design for at-line applications may be less impactful than for online applications. An active feedback probe (q switched during transmit/receive period) may be employed with low q during the transmit/probe ring down period and high q during the receiving period. Active damping should be used to improve the probe measurement characteristics, as well as to reduce the RF amplifier power requirements. As mentioned earlier, the probe dead time can impact the ultimate amount of recoverable magnetization. Probe dead times can limit both the measurement time following an RF pulse (and thus lead to reduced $M_0$ values as a consequence of reduced relaxation during the dead times) and also the minimum pulse gap/echo time ($\tau$) which leads to potential signal loss due to relaxation and diffusion effects. Unfortunately, probe dead time design is in simple probe arrangements a compromise between the shortest dead time and best signal to noise ratio. A conventional probe with high SNR also has a long dead time. Q switched probes that alter the probe electrical characteristics during the transmit/receive periods can eliminate the need for the compromise, but add to the complexity of the probe electrical circuit. Conductive samples such as ionic solutions form part of the probe tuning circuit and alter its response. If the variation in ionic concentration (conductivity) is high, then the probe can be detuned by higher concentration samples which will alter the apparent $M_0$ value. This can be compensated for by various probe electrical design techniques and though the amount of ionic concentration variation that is expected in this application will probably not lead to these effects, this can be at least considered. Standard low frequency/time domain NMR probe designs are generally less sensitive to these effects due to the electrical characteristics utilized.

Regarding the detection of $^{23}$Na specifically, this nucleus has some advantages for online/at-line NMR in the aqueous phase. When in solution, $^{23}$Na tends to exhibit relatively short $T_1$ times on the order of tens to hundreds of milliseconds. This means the repetition time/polarization time used can be short and large numbers of averages for improved SNR can be acquired in a short time. $T_2$ (s) in the aqueous phase are similar to $T_1$ (s). This is in contrast to the solid (crystalline) form, where $T_1$ (s) can be over 6000 milliseconds and $T_2$ (s) are on the order of tens of microseconds. In the aqueous phase, the relaxation of $^{23}Na$ nuclei is dominated by $^{23}Na$-$^1H$ interactions, whereas in the solid crystal $^{23}Na$-$^{23}Na$ interactions dominate, including dipolar coupling which results in a short $T_2$.

NMR of $^{23}Na$ in high resolution probes has been shown to demonstrate good quantitative results (a linear relationship between $^{23}Na$ $M_0$ and concentration). However, caution should be exhibited when extending the relationship to high concentrations, as probes can be detuned by the conductive sample in a non-linear fashion as described earlier. The probe electrical design needs to be carefully optimized so that linear $M_0$ response is observed over all anticipated $^{23}Na$ concentrations while preserving the best SNR possible. $^{23}Na$ NMR in the aqueous phase has demonstrated some $T_2$ dependence as a function of concentration. $T_2$ is presumably reduced as a result of a proximity effect to other $^{23}Na$ nuclei. This effect may need to be accommodated in online/at-line applications.

Figure 7:
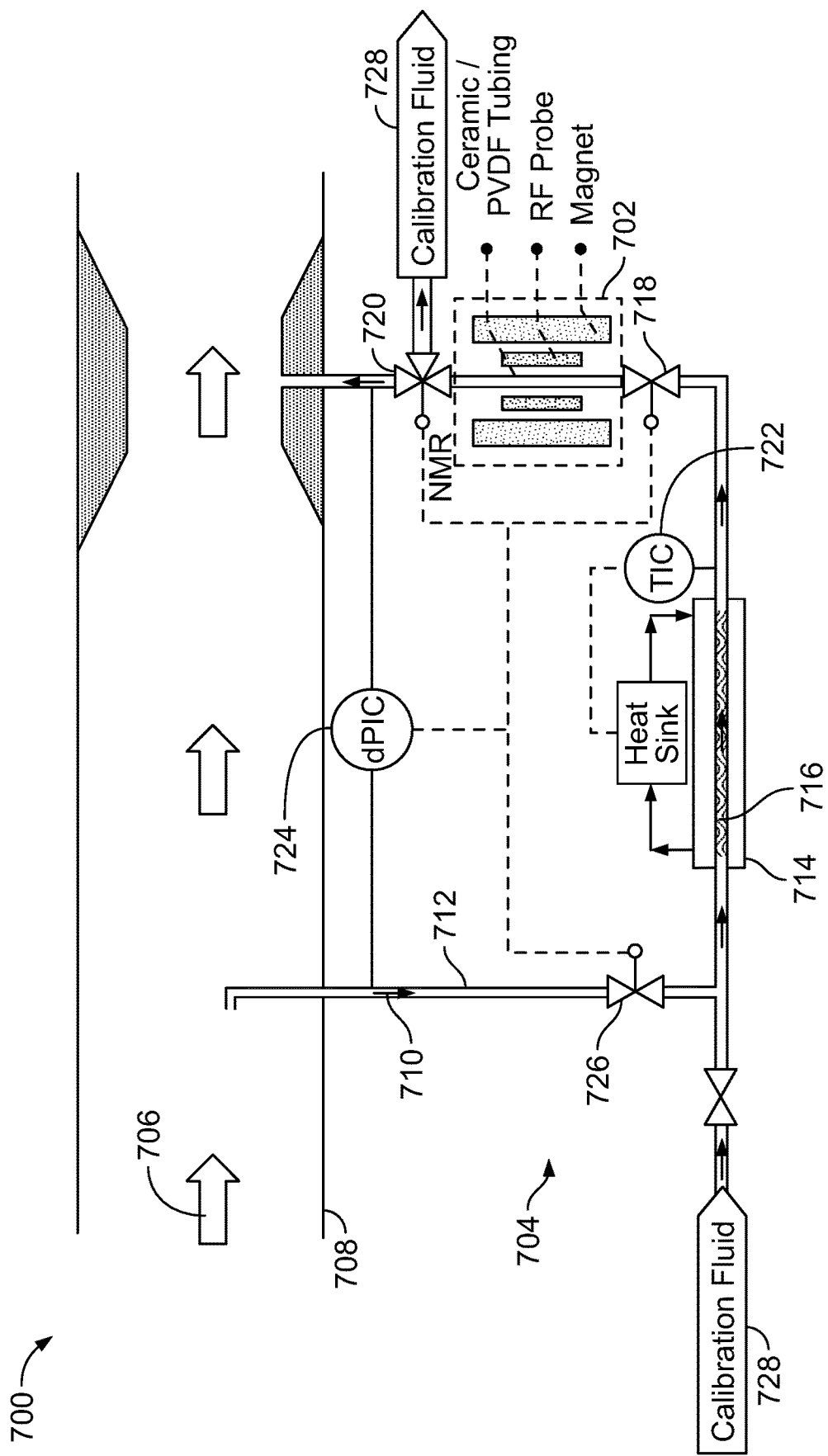
FIG. 7 is a diagram of a nuclear magnetic resonance (NMR) spectroscope system in a stop-flow configuration for sodium measurement with low-field NMR spectroscopy.

FIG. 7 is an NMR spectroscope system 700 (or NMR spectrometer system 700) in a stop-flow configuration for low-field NMR spectroscopy for sodium measurement. The example illustrated is given only as an example and not meant to limit the present techniques. The spectroscope system 700 may be configured for $^{23}Na$ NMR spectroscopy and thus labeled as a $^{23}Na$ NMR spectroscope system (or $^{23}Na$ NMR spectrometer system).

The spectroscope system 700 includes a sampling system 704 and a low-field NMR spectroscope 702 (which may be labeled as a low-field NMR spectrometer). In the illustrated embodiment, process fluid 706 flows through a process conduit 708 (pipe). In the stop-flow configuration depicted in FIG. 7, a sample 710 (slipstream) of the flowing process fluid 706 (e.g. briny water) is directed through a bypass conduit 712 (e.g., sampling conduit such as sample tubing) to an in-line heater 714 with a static mixer 716 built-in. The sample 710 is stopped and held within the low-field NMR spectroscope 702 by a set of valves 718, 720 to measure the sodium concentration in this sample 710. The sample 710 may discharge from the spectroscope 702 through the valve 720 as return to the process conduit 708.

The temperature of the sample 710 entering the NMR spectroscope 702 is slightly higher, e.g., by 5-10° C., than the process fluid 706 temperature (e.g., 30-50° C.) and controlled with a temperature transmitter (TIC) 722 or a differential temperature transmitter (dTIC) (not shown). The pressure difference between the inlet and the outlet of the bypass conduit 712 is measured via a differential-pressure indicator controller (dPIC) 724 to determine the flowrate of the sample 710 (slipstream of the process fluid 702) inside the bypass conduit 712 and to isolate/shutdown the system if there is no flow (e.g., ΔP=0). The spectroscope system 700 system may be isolated from the process, for example, by closing valve 726 and by closing valve 720 at least with respect to between the spectroscope 702 and the process conduit 708.

The NMR spectroscope system 700 can be calibrated, for example, once every year (or every quarter) to assess the potential drift of the NMR spectroscope 702. To check for the accuracy and precision of the system, the inlet valve 726 and outlet valve 720 of the bypass conduit 712 are closed. A calibration fluid 728 is passed through the NMR spectroscope 702 at a specified relevant flowrate in the same stop-flow configuration.

Figure 8:
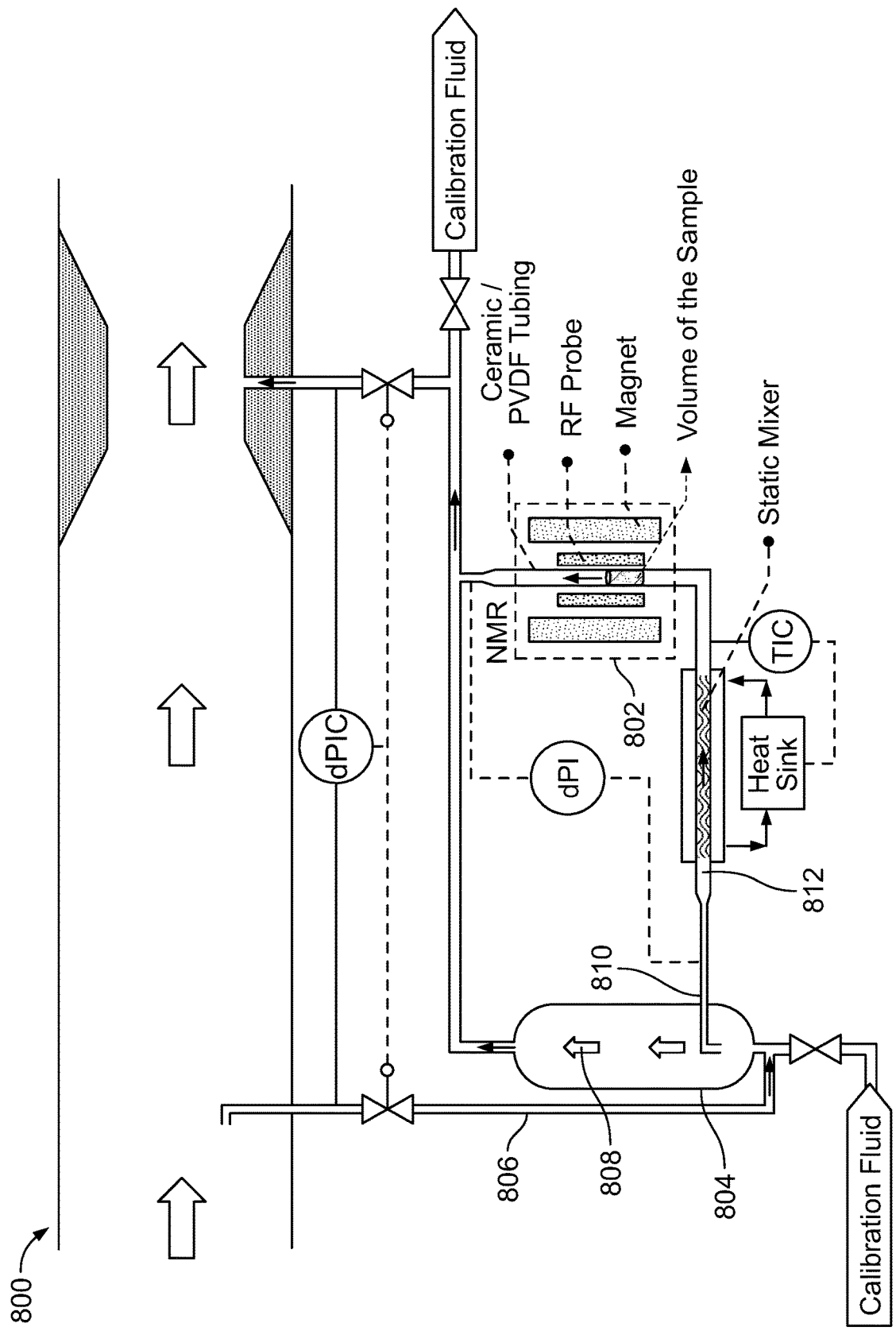
FIG. 8 is a diagram of an NMR spectroscope system in a continuous-flow configuration for sodium measurement with low-field NMR spectroscopy.

FIG. 8 is an NMR spectroscope system 800 (spectrometer system) in a continuous-flow configuration for low-field NMR spectroscopy for sodium measurement. The example illustrated is given only as an example and not meant to limit the present techniques. The NMR spectroscope system 800 has a sampling system and a low-field NMR spectroscope 802. In the continuous-flow configuration, a sample of the process fluid (e.g. briny water) is directed to a vessel 804 having larger diameter than the sampling tube 806 to slow the sampled fluid 808 (in a first stage). Then, the sampled fluid in the vessel 804 is sampled by a second sampling tube 810. This second sampling tube 810 may enlarge to a slightly larger diameter 812 to slow the sampled fluid (in a second stage).

The diameter of the second sampling tube 810 (that samples the vessel 804) may be specified to give a desired residence time of the sample fluid in the spectroscope 802. In implementations, the specified diameter for the second sampling tube 804 (before enlargement) may be, for example, ¼", ⅜", or ½", and so forth. In one example, the residence time of the fluid in an 8 centimeter (cm) RF probe is sufficient to have the same coil for the emitter and receiver without stopping the sample fluid in the spectroscope 802. This sampling fluid is generally not depressurized, which avoids possible bubble formation. Although a horizontal position of the vessel 804 (or NMR spectroscope 802) is possible (e.g., if the system is purged for perturbing bubble of air/gas), the vertical position of the vessel 804 and the NMR spectroscope 802 may be beneficial to flush any potential bubbles. In this example, the residence time in the NMR spectroscope 802 is not affected (or is slightly affected) by the production. In this example, with second sample tube 810 of diameter of ½", the residence time may vary, for instance, between 84 seconds for 16.5 thousand barrels per day (MBD) of process fluid in the main pipe of diameter 20" to 49 seconds for 28.5 MBD of process fluid (e.g., briny water) in the main pipe of diameter 20".

The pressure difference between the inlet and the outlet of the system 800 may be measured to determine the flowrate through the system 800. As with the system 700 discussed with respect to FIG. 7, the spectroscope system 800 may be isolated/shutdown if there is no flow (e.g., ΔP=0). Another differential pressure transmitter can placed between the inlet and outlet of the second sample tube 810 containing the heater and the NMR spectroscope 802 to record the flowrate of the fluid being measured. The in-line heater, with a static mixer built-in, may provide that the temperature is roughly constant with time to overcome the diurnal temperatures. The temperature of the fluid entering the NMR spectroscope 802 is slightly higher, e.g., by 5-10° C., than the process fluid temperature (30-50° C.) and controlled. The low-field NMR spectroscope 802 measures the sodium concentration contained in the sample.

Figure 9:
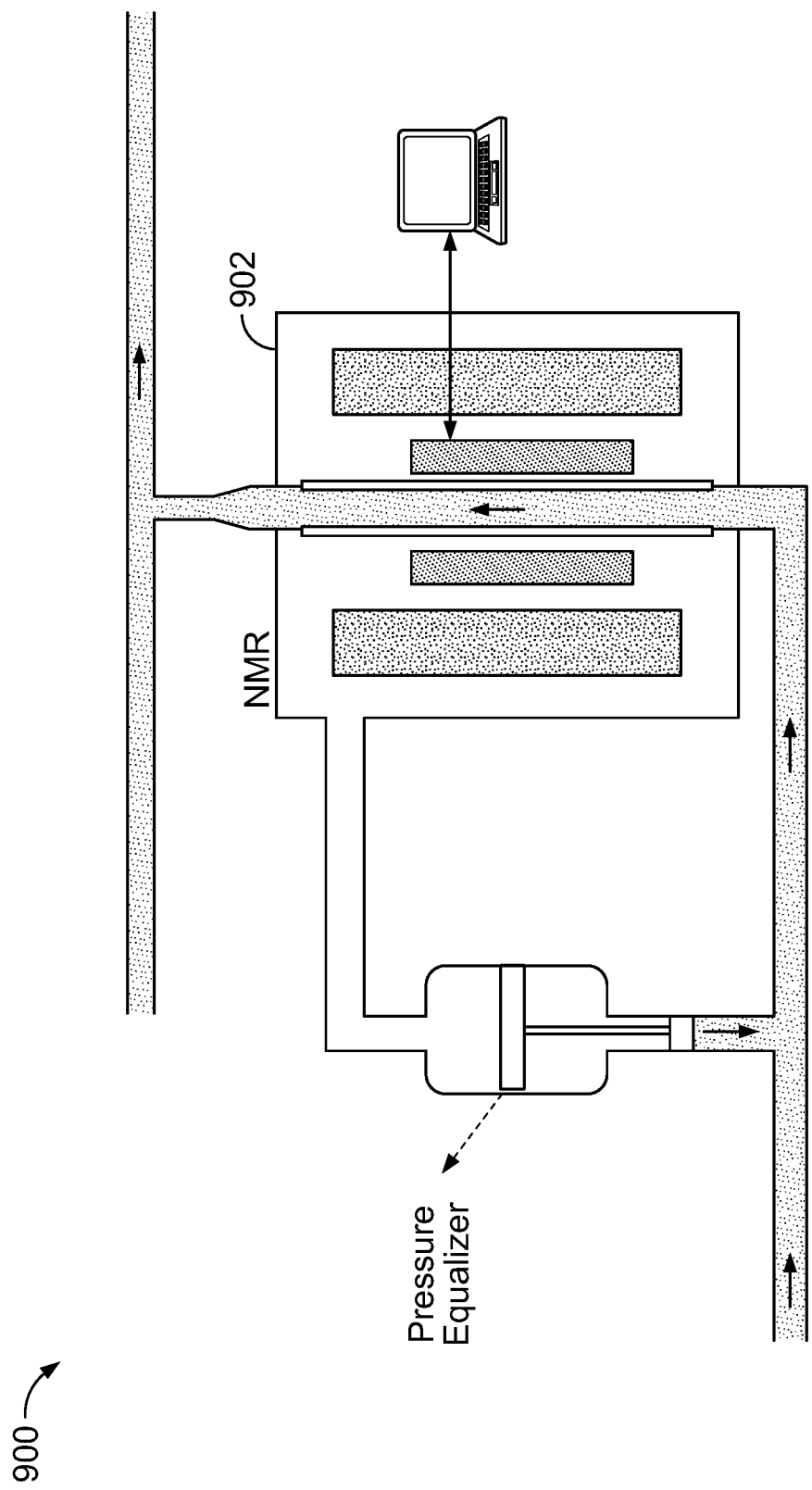
FIG. 9 is a diagram of NMR spectroscope system having a pressurized-casing around the low-field NMR spectroscope.

FIG. 9 is an NMR spectroscope system 900 implemented in a process. The NMR spectroscope system 900 having casing 902 around the low-field spectroscope. In operation, the casing 902 may be pressurized. As the low-field NMR spectroscope is in contact with a pressurized process fluid (e.g., less than 10 bar), a casing 902 protecting the magnet and RF probe may be pressurized. Oscillation of pressure in the process pipe providing the sample (as a slop stream) may be buffered via a mechanical pressure equalizer, which may maintain a relatively small difference of pressure across ceramic/polymeric tube inside the NMR casing. In addition, the casing 902 may contain fluid or system component in case of mechanical failure of the ceramic/polymeric tube inside the spectroscope.

Figure 10:
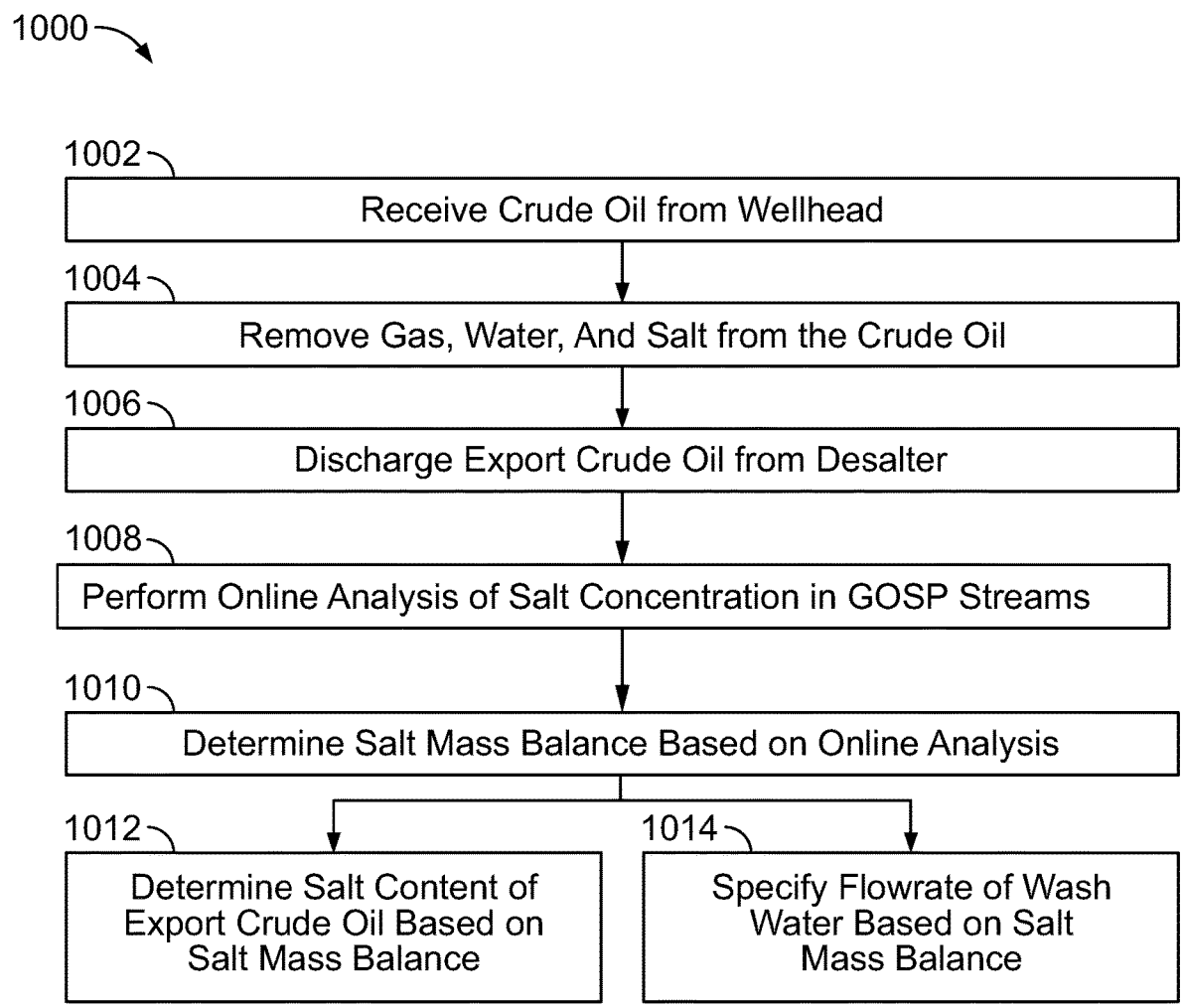
FIGS. 10-12 are block flow diagrams of methods of operating a GOSP.

FIG. 10 is a method 1000 of operating a GOSP. At block 1002, the method includes receiving crude oil from a wellhead. The crude oil received may be or include an oil-water emulsion. The crude oil received at the GOSP through a production manifold from a well. The crude oil received may be as produced from a subterranean formation through a wellbore and wellhead. The crude oil may flow through a production manifold associated with one or more wellheads to the GOSP train. The feed crude oil 102 may be from a well pool.

At block 1004, the method includes removing gas, water, and salt (e.g., NaCl) from the crude oil via a GOSP train including a first production trap, a second production trap, a dehydrator vessel, and a desalter vessel. Components of the train may operate at sequentially lower pressure to remove gas as volatile gases. In embodiments, the GOSP may include two-stage desalting involving the dehydrator vessel and the desalter vessel.

At block 1006, the method includes discharging export crude oil from the desalter vessel. The export crude oil may be crude oil as processed by the GOSP. The export crude oil may be product crude oil of the GOSP. The GOSP may discharge the export crude oil to storage or transportation for distribution.

At block 1008, the method includes performing online analysis of salt concentration in streams in the GOSP. In implementations, the online analysis of salt concentration in streams in the GOSP may include online analysis of the salt concentration in water discharged from the first production trap. The online analysis of the salt concentration in the water discharged from the first production trap may involve $^{23}$Na NMR spectroscopy. The online analysis of salt concentration in streams in the GOSP may include online analysis of the salt concentration in water discharged from the dehydrator vessel. The online analysis of the salt concentration in the water discharged from the dehydrator vessel may involve $^{23}$Na NMR spectroscopy.

The online analysis of salt concentration in streams in the GOSP may include online analysis of the salt concentration in the wash water provided to the desalter vessel. The online analysis of salt concentration in streams in the GOSP generally does not include online analysis of salt concentration in the export crude oil.

At block 1010, the method includes determining a salt mass balance of the GOSP based at least on the online analysis (block 1008). The determining of the salt mass balance may be performed in real time, such by a control system or computing system. The determining of the salt mass balance may include calculating the salt mass balance in real time based on the online analysis (block 1008) of the salt concentration. The salt mass balance may be based on additional online feedback such as flowrate from flow meters and water volume fraction from meters (e.g., density meter).

At block 1012, the method may include determining salt content of the export crude oil (e.g., in real time) based on the salt mass balance determined in block 1010. The method may include monitoring the salt content as determined and diverting the export crude oil in response to the salt content as determined not satisfying a product specification of the export crude oil.

At block 1014, the method may include specifying (e.g., in real time) the flowrate of wash water to the desalter vessel based on the salt mass balance determined in block 1010. The method may include specifying the salt content in the export crude oil for the salt mass balance.

Figure 11:
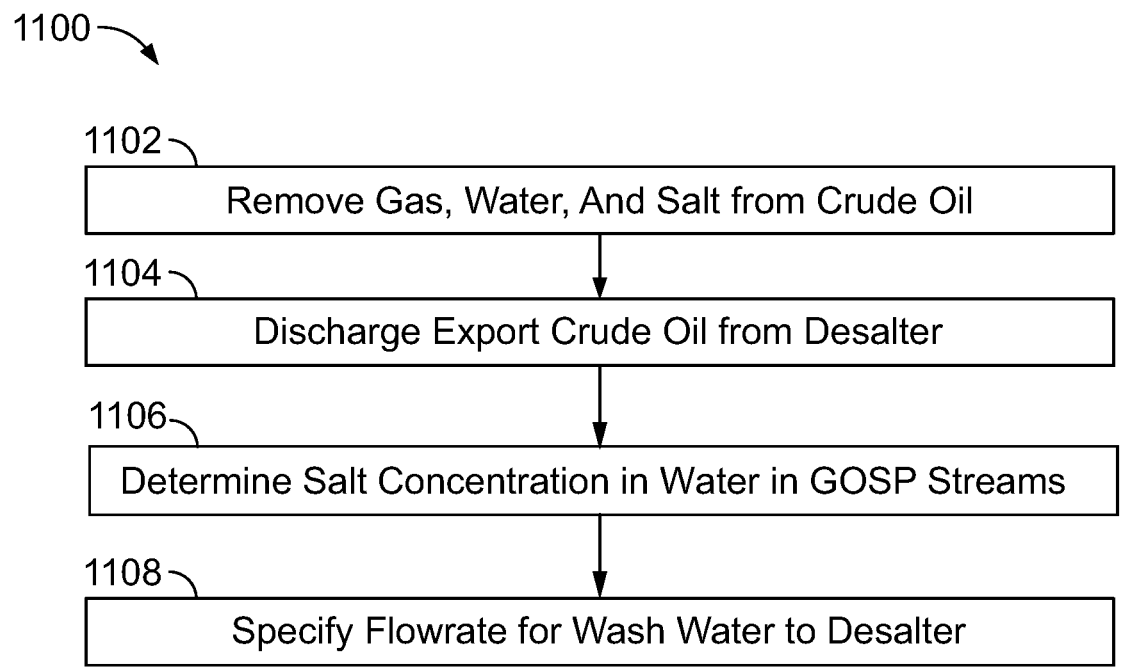

FIG. 11 is a method 1100 of operating a GOSP. The GOSP may receive crude oil from a wellhead. At block 1102, the method includes removing gas, water, and salt (e.g., NaCl) from crude oil via a GOSP train including a first production trap, a second production trap, a dehydrator vessel, and a desalter vessel.

At block 1104, the method includes discharging export crude oil from the desalter vessel. The export crude oil may be the product crude oil of the GOSP. The export crude oil may sent to storage, distribution, or transportation. The export crude oil may be further processed, such as at a petroleum refinery.

At block 1106, the method includes determining salt concentration in water in streams in the GOSP based on at least online analysis of the salt concentration in the water in the streams. The streams may include the wash-water stream provided to desalter vessel. In some implementations, the streams include at least a first stream and a second stream. For instance, the first stream may be water discharged from the first production trap, and the second stream may be water discharged from the dehydrator vessel. The online analysis of salt concentration may include performing online $^{23}$Na NMR spectroscopy on at least one of the streams.

At block 1108, the method includes specifying a flowrate for wash water supplied to the desalter vessel correlative with at least: (1) a specified salt content for the export crude oil; and (2) the salt concentration in the water in the streams as determined in block 1106. In certain implementations, the specifying of the flowrate for the wash water may involve a control system specifying a set point for a control valve (e.g., a flow control valve on the wash water supply).

Figure 12:
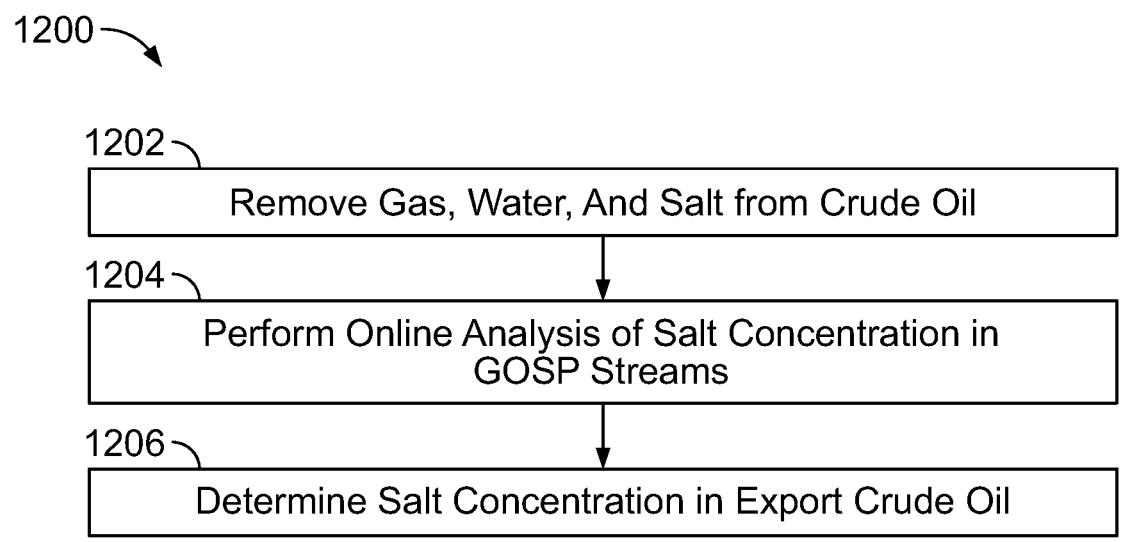

FIG. 12 is a method 1200 of operating a GOSP. At block 1202, the method includes removing gas, water, and salt (e.g., NaCl) from crude oil via a GOSP train including a first production trap, a second production trap, a dehydrator vessel, and a desalter vessel. The method may include discharging the processed crude oil as export crude oil from the desalter vessel. The export crude oil may be routed through a stabilization distillation column in some implementations.

At block 1204, the method includes performing online analysis of salt concentration on multiple streams in the GOSP. The multiple streams may include the wash-water stream provided to desalter vessel. The online analysis of salt concentration may include performing $^{23}$NMR spectroscopy on at least one of the multiple streams. In implementations, the multiple streams include a water stream discharged from the first production trap and a water stream (e.g., oil water) discharged from the dehydrator vessel. The online analysis of salt concentration on the water streams involves online analysis of the salt concentration in water in the water streams.

At block 1206, the method includes determining (e.g., in real time) salt content in export crude oil discharged from the desalter vessel correlative with at least the salt concentration for the multiple streams as determined via the online analysis. The salt content determination may incorporate additional parameters, such as flowrates of the multiple streams. The salt content in the export crude oil is generally analogous to the mathematical product of the salt concentration in water in the export crude oil multiplied by the water volume fraction of the export crude oil.

A number of implementations have been described. Nevertheless, it will be understood that various modifications may be made without departing from the spirit and scope of the disclosure.

What is claimed is:

1. A method of operating a gas oil separation plant (GOSP), the method comprising:
   receiving crude oil from a wellhead;
   removing gas, water, and salt from the crude oil via a GOSP train comprising a first production trap, a second production trap, a dehydrator vessel, and a desalter vessel, wherein the first production trap is disposed operationally upstream of the second production trap, the dehydrator vessel, and the desalter vessel, and wherein online analysis of salt concentration or salt content in export crude oil is not performed;
   operating the first production trap at a pressure greater than the second production trap;
   discharging export crude oil from the desalter vessel;
   performing online analysis of salt concentration in water streams in the GOSP, wherein the water streams comprise a first water stream discharged from the first production trap to a water/oil separator vessel;
   receiving user input to a control system of the GOSP to alternate between a first operational mode and a second operational mode;
   determining, via the control system in the first operational mode, salt content of the export crude oil based on the online analysis of salt concentration in the water streams; and
   determining, via the control system in the second operational mode, flowrate of wash water to the desalter vessel to specify based on the online analysis of salt concentration in the water streams and based on a specified salt content of the export crude oil not to exceed.

2. The method of claim 1, wherein the control system comprises a processor and memory storing code executed by the processor to perform calculations and direct operations of the GOSP, wherein the first operational mode provides for the control system automatically specifying the flowrate of wash water for the desalter vessel as determined in real time to specify for control of the salt content in the export crude oil, wherein the second operational mode provides for real-time monitoring via calculation by the control system of the salt content in the export crude oil that exits the desalter vessel, and wherein the salt comprises sodium chloride.

3. The method of claim 1, wherein online analysis of salt concentration in the crude oil is not performed.

4. The method of claim 1, wherein determining the salt content in the export crude oil in the first operational mode is performed in real time.

5. The method of claim 1, comprising monitoring the salt content of the export crude oil as determined in the first operational mode and diverting the export crude oil in response to the salt content as determined not satisfying a product specification of the export crude oil.

6. The method of claim 1, comprising equating salt concentration of brine droplets in the crude oil entering the dehydrator vessel with the salt concentration in the first water stream as determined via performing the online analysis.

7. The method of claim 1, comprising specifying the specified salt content in the export crude oil not to exceed as an input for determining the flowrate of wash water to the desalter vessel to specify in the second operational mode.

8. The method of claim 1, wherein determining the flowrate of wash water to specify in the second operational mode is performed in real time.

9. The method of claim 1, wherein the first production trap comprises a high-pressure production trap (HPPT) operating at a pressure of at least 150 pounds per square inch gauge (psig), and wherein the second production trap comprises a low-pressure production trap (LPPT) operating at a pressure less than 60 psig.

10. The method of claim 1, wherein the online analysis of the salt concentration in the first water stream comprises $^{23}$sodium ($^{23}$Na) nuclear magnetic resonance (NMR) spectroscopy comprising employing an $^{23}$Na NMR spectroscope disposed external to a conduit conveying the first water stream, and wherein a slipstream of the first water stream is routed from the conduit through sample tubing to the $^{23}$Na NMR spectroscope.

11. The method of claim 1, comprising removing, via the first production trap, gas from the crude oil comprising more C1-C4 hydrocarbons than C5+ hydrocarbons, wherein the water streams comprise a second water stream comprising water discharged from the dehydrator vessel to the water/oil separator vessel, and wherein the online analysis of the salt concentration in the second water stream is online analysis of the salt concentration in the water in the second water stream.

12. The method of claim 11, wherein the online analysis of the salt concentration in the second water stream comprises $^{23}$Na NMR spectroscopy comprising employing an $^{23}$Na NMR spectroscope disposed external to a conduit conveying the second water stream, and wherein a slipstream of the second water stream is routed from the conduit through sample tubing to the $^{23}$Na NMR spectroscope.

13. The method of claim 11, wherein the online analysis of the salt concentration in the first water stream and in the second water stream comprises $^{23}$sodium ($^{23}$Na) nuclear magnetic resonance (NMR) spectroscopy, wherein a slipstream from a first conduit conveying the first water stream is routed through first sample tubing to a first $^{23}$Na NMR spectroscope disposed external to the first conduit, wherein a slipstream from a second conduit conveying the second water stream is routed through second sample tubing to a second $^{23}$Na NMR spectroscope disposed external to the second conduit, wherein the water streams comprise a third water stream comprising the wash water provided to the desalter vessel, and wherein the flowrate of the wash water to specify as determined in the second operational mode is determined in real time based on the following equation with $\phi_{Ds}^{wi}$ being the flowrate of the wash water to specify:

$$\phi_{Ds}^{wi} = \frac{1}{\left(C_H^{wo} - C_{Ds}^{wi}\right)}[C_H^{wo}(\phi_W^{wo} - \phi_H^{wo}) + C_{Ds}^{oo} \cdot \phi_{Ds}^{oo} \cdot f_{Ds}^{oo} - C_{Dh}^{wo} \cdot \phi_{Dh}^{wo} \cdot f_{Dh}^{wo}]$$

where $C_H^{wo}$, $C_{Dh}^{wo}$, and $C_{Ds}^{wi}$ are the salt concentration of the first water stream, the second water stream, and the wash water, respectively, $C_{Ds}^{oo}$ is the specified salt content of the export crude oil not to exceed, $\phi_H^{wo}$ is flowrate of the first water stream, $\phi_{Dh}^{wo}$ flowrate of the second water stream, $\phi_{Ds}^{oo}$ is flowrate of the export crude oil discharged from the desalter vessel, $\phi_W^{wo}$ is water flowrate exiting the water/oil separator vessel, $\theta_{Dh}^{wo}$ is water volume fraction of the second water stream, and $f_{Ds}^{oo}$ is water volume fraction in the export crude oil input based on type of the export crude oil.

14. A method of operating a gas oil separation plant (GOSP), the method comprising:
   removing gas, water, and salt from crude oil via a GOSP train comprising a first production trap, a second production trap, a dehydrator vessel, and a desalter vessel, wherein the first production trap is disposed operationally upstream of the second production trap, the dehydrator vessel, and the desalter vessel;

operating the first production trap at a pressure greater than pressure in the second production trap;

discharging export crude oil from the desalter vessel;

determining salt concentration in water in streams in the GOSP based on online analysis of the salt concentration in the water in the streams, wherein the streams comprise a first stream comprising water discharged from the first production trap to a water/oil separator vessel, and wherein online analysis of salt concentration or salt content in the export crude oil is not performed;

receiving user input to a control system of the GOSP to alternate between a first operational mode and a second operational mode;

determining, via the control system in the first operational mode, salt content of the export crude oil based on the online analysis of the salt concentration in the water in the streams in the GOSP; and determining, via the control system in the second operational mode, a flowrate for wash water supplied to the desalter vessel to specify based on a specified salt content for the export crude oil and based on the online analysis of the salt concentration in the water in the streams in the GOSP, wherein determining in the first operational mode the salt content of the export crude oil and determining in the second operational mode the flowrate for the wash water to specify comprise equating salt concentration of brine droplets in the crude oil entering the dehydrator with the salt concentration in the first stream as determined based on the online analysis.

15. The method of claim 14, wherein specifying the flowrate for the wash water comprises a control system specifying a set point for a control valve, and wherein the streams do not comprise the export crude oil.

16. The method of claim 14, wherein the online analysis of the salt concentration comprises performing $^{23}$sodium ($^{23}$Na) nuclear magnetic resonance (NMR) spectroscopy comprising employing an $^{23}$Na NMR spectroscope disposed external to a conduit conveying the first stream, wherein a slipstream of the first stream is routed from the conduit through sample tubing to the $^{23}$Na NMR spectroscope, and wherein determining the salt concentration in the water in the streams based on the online analysis of the salt concentration in the water in the streams is performed in real time.

17. The method of claim 14, wherein the streams comprise a second stream comprising water discharged from the dehydrator vessel, wherein the online analysis of the salt concentration comprises performing $^{23}$Na NMR spectroscopy comprising employing an $^{23}$Na NMR spectroscope disposed external to a conduit conveying the second stream, wherein a slipstream of the second stream is routed from the conduit through sample tubing to the $^{23}$Na NMR spectroscope, and wherein specifying the flowrate comprises specifying in real time the flowrate for the wash water supplied to the desalter vessel correlative with the specified salt content for the export crude oil and correlative with the salt concentration in the water in the streams as determined.

18. The method of claim 17, wherein the streams comprise a third stream comprising the wash water supplied to the desalter vessel, wherein the first production trap comprises a high-pressure production trap (HPPT) operating at a pressure of at least 150 pounds per square inch gauge (psig), wherein the second production trap comprises a low-pressure production trap (LPPT) operating at a pressure less than 60 psig, and wherein the flowrate of the wash water to specify as determined in the second operational mode is determined in real time based on the following equation with $\phi_{Ds}^{wi}$ being the flowrate of the wash water to specify:

$$\phi_{Ds}^{wi} = \frac{1}{\left(C_H^{wo} - C_{Ds}^{wi}\right)} [C_H^{wo}(\phi_W^{wo} - \phi_H^{wo}) + C_{Ds}^{oo} \cdot \phi_{Ds}^{oo} \cdot f_{Ds}^{oo} - C_{Dh}^{wo} \cdot \phi_{Dh}^{wo} \cdot f_{Dh}^{wo}]$$

where $C_H^{wo}$, $C_{Dh}^{wo}$, and $C_{Ds}^{wi}$ are the salt concentration of the first stream, the second stream, and the third stream comprising the wash water, respectively, $C_{Ds}^{oo}$ is the specified salt content of the export crude oil, $\phi_H^{wo}$ is flowrate of the first stream, $\phi_{Dh}^{wo}$ is flowrate of the second stream, $\phi_{Ds}^{oo}$ is flowrate of the export crude oil discharged from the desalter vessel, $\phi_W^{wo}$ is water flowrate exiting the water/oil separator vessel, $f_{Dh}^{wo}$ is water volume fraction of the second stream, and $f_{Ds}^{oo}$ is water volume fraction of the export crude oil input based on type of the export crude oil.

19. A method of operating a gas oil separation plant (GOSP), the method comprising:

removing gas, water, and salt from crude oil via a GOSP train comprising a first production trap, a second production trap, a dehydrator vessel, and a desalter vessel, wherein the first production trap is disposed operationally upstream of the second production trap, the dehydrator vessel, and the desalter vessel, and wherein the first production trap operates at a higher pressure than the second production trap;

performing, in real time, online analysis of salt concentration in multiple streams in the GOSP, wherein the multiple streams comprise a first stream comprising water discharged from the first production trap to a water/oil separator vessel, and wherein the multiple streams do not comprise an export crude oil stream;

receiving user input to a control system of the GOSP to alternate between a first operational mode and a second operational mode;

determining, via the control system in real time in the first operational mode, salt content in export crude oil discharged from the desalter vessel correlative with the salt concentration in the multiple streams as determined via the online analysis; and determining, via the control system in the second operational mode, flowrate of a wash water stream to the desalter vessel to specify correlative with the salt concentration in the multiple streams as determined via the online analysis and based on a specified salt content of the export crude oil not to exceed.

20. The method of claim 19, wherein the salt content in the export crude oil comprises a product of salt concentration in water in the export crude oil multiplied by water volume fraction of the export crude oil, and wherein the salt comprises sodium chloride.

21. The method of claim 19, wherein the online analysis of salt concentration comprises performing $^{23}$sodium ($^{23}$Na) nuclear magnetic resonance (NMR) spectroscopy comprising employing an $^{23}$Na NMR spectroscope disposed external to a conduit conveying the first stream, and wherein a slipstream of the first stream is routed from the conduit through sample tubing to the $^{23}$Na NMR spectroscope.

22. The method of claim 19, wherein determining, in real time, the salt content in the export crude oil discharged from the desalter vessel correlative with the salt concentration in the multiple streams as determined via the online analysis comprises equating salt concentration of brine droplets in the crude oil entering the dehydrator with the salt concentration in the first stream as determined via the online analysis.

23. The method of claim 19, wherein the multiple streams comprise a second stream comprising an oily water stream discharged from the dehydrator vessel, wherein online analysis of salt concentration in the second stream is online analysis of the salt concentration in water in the second stream, wherein the online analysis of the salt concentration in the first stream and in the second stream comprises $^{23}$sodium ($^{23}$Na) nuclear magnetic resonance (NMR) spectroscopy, wherein a slipstream from a first conduit conveying the first stream is routed through first sample tubing to a first $^{23}$Na NMR spectroscope disposed external to the first conduit, and wherein a slipstream from a second conduit conveying the second stream is routed through second sample tubing to a second $^{23}$Na NMR spectroscope disposed external to the second conduit.

24. The method of claim 23, wherein the multiple streams comprise the wash water stream provided to the desalter vessel, wherein the first production trap comprises a high-pressure production trap (HPPT) operating at a pressure of at least 150 pounds per square inch gauge (psig), wherein the second production trap comprises a low-pressure production trap (LPPT) operating at a pressure less than 60 psig, and wherein the flowrate of the wash water stream to specify as determined in the second operational mode is determined in real time based on the following equation with $\phi_{Ds}^{wi}$ being the flowrate of the wash water stream to specify:

$$\phi_{Ds}^{wi} = \frac{1}{\left(C_H^{wo} - C_{Ds}^{wi}\right)} [C_H^{wo}(\phi_W^{wo} - \phi_H^{wo}) + C_{Ds}^{oo} \cdot \phi_{Ds}^{oo} \cdot f_{Ds}^{oo} - C_{Dh}^{wo} \cdot \phi_{Dh}^{wo} \cdot f_{Dh}^{wo}]$$

where $C_H^{wo}$, $C_{Dh}^{wo}$, and $C_{Ds}^{wi}$ are the salt concentration of the first stream, the second stream, and the wash water stream, respectively, $C_{Ds}^{oo}$ is the specified salt content of the export crude oil, $\phi_H^{wo}$ is flowrate of the first stream, $\phi_{Dh}^{wo}$ is flowrate of the second stream, $\phi_{Ds}^{oo}$ is flowrate of the export crude oil discharged from the desalter vessel, $\phi_W^{wo}$ is water flowrate exiting the water/oil separator vessel, $f_{Dh}^{wo}$ is water volume fraction of the second stream, and $f_{Ds}^{oo}$ is water volume fraction of the export crude oil input based on type of the export crude oil.

\* \* \* \* \*